United States Patent
Feldman et al.

(10) Patent No.: US 9,359,447 B2
(45) Date of Patent: Jun. 7, 2016

(54) ANTI-MESOTHELIN CHIMERIC ANTIGEN RECEPTORS

(71) Applicant: The United States of America, as represented by the Secretary, Department of Health and Human Services, Washington, DC (US)

(72) Inventors: Steven A. Feldman, Washington, DC (US); Steven A. Rosenberg, Potomac, MD (US); Ira H. Pastan, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 25 days.

(21) Appl. No.: 14/384,282

(22) PCT Filed: Mar. 5, 2013

(86) PCT No.: PCT/US2013/028980
§ 371 (c)(1),
(2) Date: Sep. 10, 2014

(87) PCT Pub. No.: WO2013/142034
PCT Pub. Date: Sep. 26, 2013

(65) Prior Publication Data
US 2015/0031624 A1    Jan. 29, 2015

Related U.S. Application Data

(60) Provisional application No. 61/614,612, filed on Mar. 23, 2012.

(51) Int. Cl.
| C07K 16/46 | (2006.01) |
| A61K 47/48 | (2006.01) |
| C07K 14/725 | (2006.01) |
| C07K 14/705 | (2006.01) |
| C07K 16/30 | (2006.01) |
| C07K 14/715 | (2006.01) |
| G01N 33/574 | (2006.01) |

(52) U.S. Cl.
CPC ............ *C07K 16/46* (2013.01); *A61K 47/48569* (2013.01); *C07K 14/7051* (2013.01); *C07K 14/70517* (2013.01); *C07K 14/70521* (2013.01); *C07K 14/70578* (2013.01); *C07K 14/7153* (2013.01); *C07K 16/30* (2013.01); *G01N 33/574* (2013.01); *G01N 33/57407* (2013.01); *G01N 33/57423* (2013.01); *G01N 33/57438* (2013.01); *G01N 33/57446* (2013.01); *G01N 33/57449* (2013.01); *C07K 2317/60* (2013.01); *C07K 2317/622* (2013.01); *C07K 2319/00* (2013.01); *C07K 2319/02* (2013.01); *C07K 2319/03* (2013.01); *C07K 2319/33* (2013.01)

(58) Field of Classification Search
CPC ...................................................... C07K 16/46
See application file for complete search history.

(56) References Cited

U.S. PATENT DOCUMENTS

| 3,832,253 | A | 8/1974 | Palma et al. |
| 3,854,480 | A | 12/1974 | Zaffaroni |
| 4,235,871 | A | 11/1980 | Papahadjopoulos et al. |
| 4,450,150 | A | 5/1984 | Sidman |
| 4,452,775 | A | 6/1984 | Kent |
| 4,501,728 | A | 2/1985 | Geho et al. |
| 4,667,014 | A | 5/1987 | Nestor et al. |
| 4,748,034 | A | 5/1988 | Rham |
| 4,837,028 | A | 6/1989 | Allen |
| 5,019,369 | A | 5/1991 | Presant et al. |
| 5,075,109 | A | 12/1991 | Tice et al. |
| 5,087,616 | A | 2/1992 | Myers et al. |
| 5,225,539 | A | 7/1993 | Winter |
| 5,239,660 | A | 8/1993 | Ooi |
| 5,449,752 | A | 9/1995 | Fujii et al. |
| 5,545,806 | A | 8/1996 | Lonberg et al. |
| 5,569,825 | A | 10/1996 | Lonberg et al. |
| 5,585,089 | A | 12/1996 | Queen et al. |
| 5,639,641 | A | 6/1997 | Pedersen et al. |
| 5,693,761 | A | 12/1997 | Queen et al. |
| 5,714,352 | A | 2/1998 | Jakobobits et al. |

(Continued)

FOREIGN PATENT DOCUMENTS

| EP | 0 239 400 B1 | 8/1994 |
| GB | 2 188 638 A | 10/1987 |

(Continued)

OTHER PUBLICATIONS

Carpenito et al., 2009, PNAS, 106(9): 3360-3365.*

(Continued)

*Primary Examiner* — Amber D Steele
(74) *Attorney, Agent, or Firm* — Leydig, Voit & Mayer

(57) ABSTRACT

The invention provides a chimeric antigen receptor (CAR) (a) an antigen binding domain of HN1 or SS, a transmembrane domain, and an intracellular T cell signaling domain, or (b) an antigen binding domain of SS1, a transmembrane domain, an intracellular T cell signaling domain, and a granulocyte-macrophage colony-stimulating factor (GM-CSF) receptor 2 leader. Nucleic acids, recombinant expression vectors, host cells, populations of cells, antibodies, or antigen binding portions thereof, and pharmaceutical compositions relating to the CARs are disclosed. Methods of detecting the presence of cancer in a mammal and methods of treating or preventing cancer in a mammal are also disclosed.

27 Claims, 2 Drawing Sheets

(56) References Cited

U.S. PATENT DOCUMENTS

Figure 1:
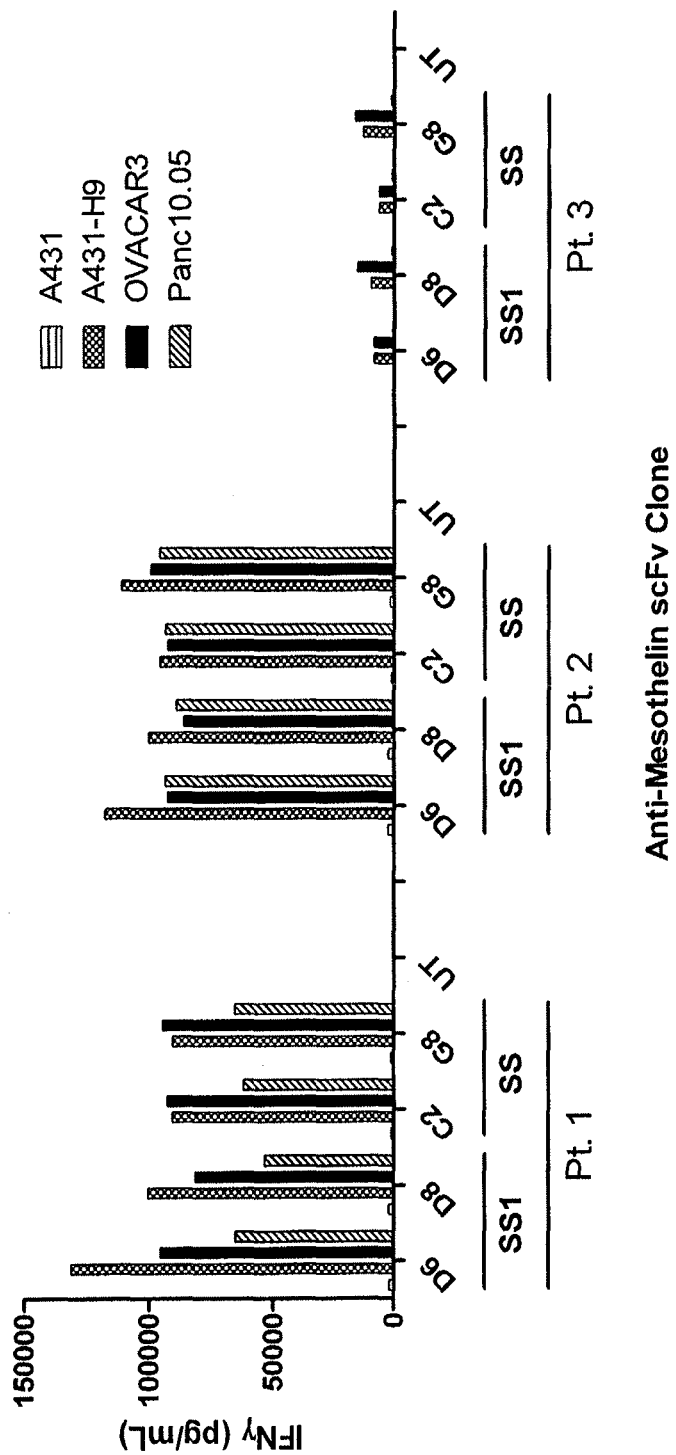

| | | | |
|---|---|---|---|
| 6,265,150 | B1 | 7/2001 | Terstappen et al. |
| 6,809,184 | B1 | 10/2004 | Pastan et al. |
| 7,081,518 | B1 | 7/2006 | Pastan et al. |
| 7,338,929 | B2 | 3/2008 | Debinski et al. |
| 7,592,426 | B2 | 9/2009 | Ebel et al. |
| 7,709,252 | B2 | 5/2010 | Pastan et al. |
| 7,943,133 | B2 | 5/2011 | Gelfand |
| 2002/0197266 | A1 | 12/2002 | Debinski |
| 2009/0257991 | A1 | 10/2009 | Li et al. |
| 2010/0105136 | A1 | 4/2010 | Carter et al. |

FOREIGN PATENT DOCUMENTS

| | | | |
|---|---|---|---|
| WO | WO 00/73346 | A1 | 12/2000 |
| WO | WO 2008/121420 | A1 | 10/2008 |
| WO | WO 2009/091826 | A1 | 7/2009 |
| WO | WO 2010/111282 | A1 | 9/2010 |
| WO | WO 2012/079000 | A1 | 6/2012 |
| WO | WO 2012/138475 | A1 | 10/2012 |
| WO | WO 2013/063419 | A2 | 5/2013 |

OTHER PUBLICATIONS

Capecchi, M., "High efficiency transformation by direct microinjection of DNA into cultured mammalian cells," *Cell*, 22, 479-88 (1980).

Carpenito et al., "Control of large, established tumor xenografts with genetically retargeted human T cells containing CD28 and CD137 domains," *Proc. Natl. Acad. Sci.*, 106 (9), 3360-65 (2009).

Chu et al., "SV40 DNA transfection of cells in suspension: analysis of the efficiency of transcription and translation of T-antigen," *Gene*, 13, 197-202 (1981).

Clay et al., "Efficient transfer of a tumor antigen-reactive TCR to human peripheral blood lymphocytes confers anti-tumor reactivity," *J. Immunol.*, 163, 507-13 (1999).

Dudley et al., "T-cell clones from melanoma patients immunized against an anchor-modified gp100 peptide display discordant effector phenotypes," *Cancer journal*, 6 (2), 69-77 (2000).

Felgner et al., "Lipofection: A highly efficient, lipid-mediated DNA-transfection procedure," *PNAS*, 84, 7413-14 (1987).

Graham et al., "A new technique for the assay of infectivity of human adenovirus 5 DNA," *Virology*, 52, 456-67 (1973).

Haskard et al., "The production of human monoclonal autoantibodies from patients with rheumatoid arthritis by the ebv-hybridoma technique," *J. Immunol. Methods*, 74, 361-7 (1984).

Hudecz, F., "Synthesis of peptide bioconjugates," *Methods Mol. Biol.*, 298, 209-23 (2005).

Huse et al., "Generation of a large combinatorial library of the immunoglobulin repertoire in phage lambda," *Science*, 246, 1275-81 (1989).

International Search Report, Application No. PCT/US2013/028980 mailed Jun. 24, 2013.

Kirin et al., "Amino acid and peptide bioconjugates of copper(II) and zinc(II) complexes with a modified N,N-Bis(2-picolyl)amine ligand," *Inorganic Chem.*, 44(15), 5405-15 (2005).

Klein et al., "High-velocity microprojectiles for delivering nucleic acids into living cells," *Nature*, 327, 70-73 (1987).

Köhler et al., "Derivation of specific antibody-producing tissue culture and tumor lines by cell fusion," *Eur. J. Immunol.*, 6(7), 511-19 (1976).

Lanitis et al., "Redirected Antitumor Activity of Primary Human Lymphocytes Transduced With a Fully Human Anti-mesothelin Chimeric Receptor," *Mol. Ther.*, 20(3): 633-643 (published online Nov. 29, 2011).

Mannino et al., "Liposome mediated gene transfer," *BioTechniques*, 6, 682-90 (1988).

Moon et al., "Expression of a Functional CCR2 Receptor Enhances Tumor Localization and Tumor Eradication by Retargeted Human T cells Expressing a Mesothelin-Specific Chimeric Antibody Receptor," *Clin. Cancer Res.*, 17(14): 4719-30 (2011).

Pedersen et al., "Comparison of surface accessible residues in human and murine immunoglobulin fv domains," *J. Mol. Biol.*, 235, 959-73 (1994).

Reiter et al., "An antibody single-domain phage display library of a native heavy chain variable region: isolation of functional single-domain VH molecules with a unique interface," *J. Mol. Biol.*, 290, 685-698 (1999).

Reiter et al., Engineering interchain disulfide bonds into conserved framework regions of Fv fragments: improved biochemical characteristics of recombinant immunotoxins containing disulfide-stabilized Fv, *Protein Eng.*, 7(5): 697-704 (1994).

Riddell et al., "Restoration of viral immunity in immunodeficient humans by the adoptive transfer of T cell clones," Science, 257, 238-241 (1992).

Roder et al., "The EBV-hybridoma technique," *Methods Enzymol.*, 121, 140-167 (1986).

Shigekawa et al., "Electroporation of eukaryotes and prokaryotes: a general approach to the introduction of macromolecules into cells," *BioTechniques*, 6, 742-51 (1980).

Szoka et al., "Comparative properties and methods of preparation of lipid vesicles (liposomes)," *Ann. Rev. Biophys. Bioeng.*, 9, 467 (1980).

Wadhwa et al., "Receptor mediated glycotargeting," *J. Drug Targeting*, 3, 111-27 (1995).

Wang et al., "A transgene-encoded cell surface polypeptide for selection, in vivo tracking, and ablation of engineered cells," *Blood.*, 118(5): 1255-1263 (2011).

Written Opinion, International Application No. PCT/US2013/028980 dated Jun. 24, 2013.

Zhao et al., "Multiple Injections of Electroporated Autologous T Cells Expressing a Chimeric Antigen Receptor Mediate Regression of Human Disseminated Tumor," *Cancer Res.*, 70(22): 9053-61 (2010).

Zhao et al., "Primary human lymphocytes transduced with NY-ESO-1 antigen-specific TCR genes recognize and kill diverse human tumor cell liner," *J. Immunol.*, 174, 4415-23 (2005).

\* cited by examiner

SEQUENCE LISTING

```
<160> NUMBER OF SEQ ID NOS: 32

<210> SEQ ID NO 1
<211> LENGTH: 106
<212> TYPE: PRT
<213> ORGANISM: Artificial Sequence
<220> FEATURE:
<223> OTHER INFORMATION: Light chain scFv SS

<400> SEQUENCE: 1

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Gly Tyr Pro Leu Thr
                85                  90                  95

Phe Gly Ala Gly Thr Lys Leu Glu Ile Lys
            100                 105

<210> SEQ ID NO 2
<211> LENGTH: 106
<212> TYPE: PRT
<213> ORGANISM: Artificial Sequence
<220> FEATURE:
<223> OTHER INFORMATION: Light chain scFv SS1

<400> SEQUENCE: 2

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ala Gly Thr Lys Leu Glu Ile Lys
            100                 105

<210> SEQ ID NO 3
<211> LENGTH: 108
<212> TYPE: PRT
<213> ORGANISM: Artificial Sequence
<220> FEATURE:
<223> OTHER INFORMATION: Light chain scFv HN1
```

<400> SEQUENCE: 3

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys Arg
            100                 105

<210> SEQ ID NO 4
<211> LENGTH: 119
<212> TYPE: PRT
<213> ORGANISM: Artificial Sequence
<220> FEATURE:
<223> OTHER INFORMATION: Heavy chain scFv SS

<400> SEQUENCE: 4

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser
        115

<210> SEQ ID NO 5
<211> LENGTH: 119
<212> TYPE: PRT
<213> ORGANISM: Artificial Sequence
<220> FEATURE:
<223> OTHER INFORMATION: Heavy chain scFv SS1

<400> SEQUENCE: 5

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser
        115

<210> SEQ ID NO 6
<211> LENGTH: 120
<212> TYPE: PRT
<213> ORGANISM: Artificial Sequence
<220> FEATURE:
<223> OTHER INFORMATION: Heavy chain scFv HN1

<400> SEQUENCE: 6

Ala Gln Val Gln Leu Val Gln Ser Gly Ala Glu Val Lys Arg Pro Gly
1               5                   10                  15

Ala Ser Val Gln Val Ser Cys Arg Ala Ser Gly Tyr Ser Ile Asn Thr
            20                  25                  30

Tyr Tyr Met Gln Trp Val Arg Gln Ala Pro Gly Ala Gly Leu Glu Trp
        35                  40                  45

Met Gly Val Ile Asn Pro Ser Gly Val Thr Ser Tyr Ala Gln Lys Phe
    50                  55                  60

Gln Gly Arg Val Thr Leu Thr Asn Asp Thr Ser Thr Asn Thr Val Tyr
65                  70                  75                  80

Met Gln Leu Asn Ser Leu Thr Ser Ala Asp Thr Ala Val Tyr Tyr Cys
                85                  90                  95

Ala Arg Trp Ala Leu Trp Gly Asp Phe Gly Met Asp Val Trp Gly Lys
            100                 105                 110

Gly Thr Leu Val Thr Val Ser Ser
        115                 120

<210> SEQ ID NO 7
<211> LENGTH: 15
<212> TYPE: PRT
<213> ORGANISM: Artificial Sequence
<220> FEATURE:
<223> OTHER INFORMATION: Linker

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Linker

<400> SEQUENCE: 8

Gly Gly Gly Gly Ser Gly Gly Gly Gly Ser Ser Gly Gly Gly Ser
1               5                   10                  15

<210> SEQ ID NO 9
<211> LENGTH: 25
<212> TYPE: PRT
<213> ORGANISM: Artificial Sequence
<220> FEATURE:

-continued

<223> OTHER INFORMATION: GM-CSF leader

<400> SEQUENCE: 9

Met Val Leu Leu Val Thr Ser Leu Leu Cys Glu Leu Pro His Pro
1               5                   10                  15

Ala Phe Leu Leu Ile Pro Asp Ile Gln
            20                  25

<210> SEQ ID NO 10
<211> LENGTH: 267
<212> TYPE: PRT
<213> ORGANISM: Artificial Sequence
<220> FEATURE:
<223> OTHER INFORMATION: SS scFv

<400> SEQUENCE: 10

Met Val Leu Leu Val Thr Ser Leu Leu Cys Glu Leu Pro His Pro
1               5                   10                  15

Ala Phe Leu Leu Ile Pro Asp Ile Gln Gln Val Gln Leu Gln Gln Ser
            20                  25                  30

Gly Pro Glu Leu Glu Lys Pro Gly Ala Ser Val Lys Ile Ser Cys Lys
        35                  40                  45

Ala Ser Gly Tyr Ser Phe Thr Gly Tyr Thr Met Asn Trp Val Lys Gln
    50                  55                  60

Ser His Gly Lys Ser Leu Glu Trp Ile Gly Leu Ile Thr Pro Tyr Asn
65                  70                  75                  80

Gly Ala Ser Ser Tyr Asn Gln Lys Phe Arg Gly Lys Ala Thr Leu Thr
                85                  90                  95

Val Asp Lys Ser Ser Thr Ala Tyr Met Asp Leu Leu Ser Leu Thr
            100                 105                 110

Ser Glu Asp Ser Ala Val Tyr Phe Cys Ala Arg Gly Gly Tyr Asp Gly
        115                 120                 125

Arg Gly Phe Asp Tyr Trp Gly Gln Gly Thr Thr Val Thr Val Ser Ser
    130                 135                 140

Gly Gly Gly Gly Ser Gly Gly Gly Ser Gly Gly Gly Gly Ser Asp
145                 150                 155                 160

Ile Glu Leu Thr Gln Ser Pro Ala Ile Met Ser Ala Ser Pro Gly Glu
                165                 170                 175

Lys Val Thr Met Thr Cys Ser Ala Ser Ser Val Ser Tyr Met His
            180                 185                 190

Trp Tyr Gln Gln Lys Ser Gly Thr Ser Pro Lys Arg Trp Ile Tyr Asp
        195                 200                 205

Thr Ser Lys Leu Ala Ser Gly Val Pro Gly Arg Phe Ser Gly Ser Gly
    210                 215                 220

Ser Gly Asn Ser Tyr Ser Leu Thr Ile Ser Ser Val Glu Ala Glu Asp
225                 230                 235                 240

Asp Ala Thr Tyr Tyr Cys Gln Gln Trp Ser Gly Tyr Pro Leu Thr Phe
                245                 250                 255

Gly Ala Gly Thr Lys Leu Glu Ile Lys Ala Ala
            260                 265

<210> SEQ ID NO 11
<211> LENGTH: 265
<212> TYPE: PRT
<213> ORGANISM: Artificial Sequence
<220> FEATURE:
<223> OTHER INFORMATION: SS1 scFv

<400> SEQUENCE: 11

Met Val Leu Leu Val Thr Ser Leu Leu Leu Cys Glu Leu Pro His Pro
1               5                   10                  15

Ala Phe Leu Leu Ile Pro Asp Ile Gln Gln Val Gln Leu Gln Gln Ser
                20                  25                  30

Gly Pro Glu Leu Glu Lys Pro Gly Ala Ser Val Lys Ile Ser Cys Lys
            35                  40                  45

Ala Ser Gly Tyr Ser Phe Thr Gly Tyr Thr Met Asn Trp Val Lys Gln
        50                  55                  60

Ser His Gly Lys Ser Leu Glu Trp Ile Gly Leu Ile Thr Pro Tyr Asn
65                  70                  75                  80

Gly Ala Ser Ser Tyr Asn Gln Lys Phe Arg Gly Lys Ala Thr Leu Thr
                85                  90                  95

Val Asp Lys Ser Ser Ser Thr Ala Tyr Met Asp Leu Leu Ser Leu Thr
                100                 105                 110

Ser Glu Asp Ser Ala Val Tyr Phe Cys Ala Arg Gly Gly Tyr Asp Gly
            115                 120                 125

Arg Gly Phe Asp Tyr Trp Gly Gln Gly Thr Thr Val Thr Val Ser Ser
    130                 135                 140

Gly Gly Gly Gly Ser Gly Gly Gly Ser Gly Gly Gly Ser Asp
145                 150                 155                 160

Ile Glu Leu Thr Gln Ser Pro Ala Ile Met Ser Ala Ser Pro Gly Glu
                165                 170                 175

Lys Val Thr Met Thr Cys Ser Ala Ser Ser Ser Val Ser Tyr Met His
            180                 185                 190

Trp Tyr Gln Gln Lys Ser Gly Thr Ser Pro Lys Arg Trp Ile Tyr Asp
        195                 200                 205

Thr Ser Lys Leu Ala Ser Gly Val Pro Gly Arg Phe Ser Gly Ser Gly
    210                 215                 220

Ser Gly Asn Ser Tyr Ser Leu Thr Ile Ser Ser Val Glu Ala Glu Asp
225                 230                 235                 240

Asp Ala Thr Tyr Tyr Cys Gln Gln Trp Ser Lys His Pro Leu Thr Phe
                245                 250                 255

Gly Ala Gly Thr Lys Leu Glu Ile Lys
                260                 265

<210> SEQ ID NO 12
<211> LENGTH: 268
<212> TYPE: PRT
<213> ORGANISM: Artificial Sequence
<220> FEATURE:
<223> OTHER INFORMATION: HN1 scFv

<400> SEQUENCE: 12

Met Val Leu Leu Val Thr Ser Leu Leu Leu Cys Glu Leu Pro His Pro
1               5                   10                  15

Ala Phe Leu Leu Ile Pro Asp Ile Gln Ala Gln Val Gln Leu Val Gln
                20                  25                  30

Ser Gly Ala Glu Val Lys Arg Pro Gly Ala Ser Val Gln Val Ser Cys
            35                  40                  45

Arg Ala Ser Gly Tyr Ser Ile Asn Thr Tyr Tyr Met Gln Trp Val Arg
        50                  55                  60

Gln Ala Pro Gly Ala Gly Leu Glu Trp Met Gly Val Ile Asn Pro Ser
65                  70                  75                  80

Gly Val Thr Ser Tyr Ala Gln Lys Phe Gln Gly Arg Val Thr Leu Thr

```
                        85                  90                  95
Asn Asp Thr Ser Thr Asn Thr Val Tyr Met Gln Leu Asn Ser Leu Thr
                100                 105                 110

Ser Ala Asp Thr Ala Val Tyr Tyr Cys Ala Arg Trp Ala Leu Trp Gly
            115                 120                 125

Asp Phe Gly Met Asp Val Trp Gly Lys Gly Thr Leu Val Thr Val Ser
        130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
                180                 185                 190

Leu Ala Trp Tyr Gln Gln Lys Pro Gly Lys Ala Pro Lys Leu Leu Ile
            195                 200                 205

Tyr Lys Ala Ser Ser Leu Ala Ser Gly Ala Pro Ser Arg Phe Ser Gly
        210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg
            260                 265

<210> SEQ ID NO 13
<211> LENGTH: 86
<212> TYPE: PRT
<213> ORGANISM: Artificial Sequence
<220> FEATURE:
<223> OTHER INFORMATION: CD8 TM domain

<400> SEQUENCE: 13

Ala Ala Ala Phe Val Pro Val Phe Leu Pro Ala Lys Pro Thr Thr Thr
1               5                   10                  15

Pro Ala Pro Arg Pro Pro Thr Pro Ala Pro Thr Ile Ala Ser Gln Pro
            20                  25                  30

Leu Ser Leu Arg Pro Glu Ala Cys Arg Pro Ala Ala Gly Gly Ala Val
        35                  40                  45

His Thr Arg Gly Leu Asp Phe Ala Cys Asp Ile Tyr Ile Trp Ala Pro
    50                  55                  60

Leu Ala Gly Thr Cys Gly Val Leu Leu Leu Ser Leu Val Ile Thr Leu
65                  70                  75                  80

Tyr Cys Asn His Arg Asn
                85

<210> SEQ ID NO 14
<211> LENGTH: 67
<212> TYPE: PRT
<213> ORGANISM: Artificial Sequence
<220> FEATURE:
<223> OTHER INFORMATION: CD28 TM domain

<400> SEQUENCE: 14

Ala Ile Glu Val Met Tyr Pro Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30
```

```
Leu Phe Pro Gly Pro Ser Lys Pro Phe Trp Val Leu Val Val Gly
        35                  40                  45

Gly Val Leu Ala Cys Tyr Ser Leu Leu Val Thr Val Ala Phe Ile Ile
 50                  55                  60

Phe Trp Val
 65

<210> SEQ ID NO 15
<211> LENGTH: 41
<212> TYPE: PRT
<213> ORGANISM: Artificial Sequence
<220> FEATURE:
<223> OTHER INFORMATION: CD28 intracellular T cell signaling domain

<400> SEQUENCE: 15

Arg Ser Lys Arg Ser Arg Leu Leu His Ser Asp Tyr Met Asn Met Thr
 1               5                  10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 16
<211> LENGTH: 47
<212> TYPE: PRT
<213> ORGANISM: Artificial Sequence
<220> FEATURE:
<223> OTHER INFORMATION: CD137 intracellular T cell signaling domain

<400> SEQUENCE: 16

Arg Phe Ser Val Val Lys Arg Gly Arg Lys Lys Leu Leu Tyr Ile Phe
 1               5                  10                  15

Lys Gln Pro Phe Met Arg Pro Val Gln Thr Thr Gln Glu Glu Asp Gly
                20                  25                  30

Cys Ser Cys Arg Phe Pro Glu Glu Glu Glu Gly Gly Cys Glu Leu
            35                  40                  45

<210> SEQ ID NO 17
<211> LENGTH: 112
<212> TYPE: PRT
<213> ORGANISM: Artificial Sequence
<220> FEATURE:
<223> OTHER INFORMATION: CD3 zeta intracellular T cell signaling domain

<400> SEQUENCE: 17

Arg Val Lys Phe Ser Arg Ser Ala Asp Ala Pro Ala Tyr Gln Gln Gly
 1               5                  10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

<210> SEQ ID NO 18
<211> LENGTH: 487
<212> TYPE: PRT
<213> ORGANISM: Artificial Sequence
<220> FEATURE:
<223> OTHER INFORMATION: SSscFv-CD28Z CAR

<400> SEQUENCE: 18

```
Met Val Leu Val Thr Ser Leu Leu Cys Glu Leu Pro His Pro
1               5                   10                  15

Ala Phe Leu Leu Ile Pro Asp Ile Gln Val Gln Leu Gln Gln Ser
            20                  25                  30

Gly Pro Glu Leu Glu Lys Pro Gly Ala Ser Val Lys Ile Ser Cys Lys
        35                  40                  45

Ala Ser Gly Tyr Ser Phe Thr Gly Tyr Thr Met Asn Trp Val Lys Gln
    50                  55                  60

Ser His Gly Lys Ser Leu Glu Trp Ile Gly Leu Ile Thr Pro Tyr Asn
65                  70                  75                  80

Gly Ala Ser Ser Tyr Asn Gln Lys Phe Arg Gly Lys Ala Thr Leu Thr
                85                  90                  95

Val Asp Lys Ser Ser Ser Thr Ala Tyr Met Asp Leu Leu Ser Leu Thr
            100                 105                 110

Ser Glu Asp Ser Ala Val Tyr Phe Cys Ala Arg Gly Gly Tyr Asp Gly
        115                 120                 125

Arg Gly Phe Asp Tyr Trp Gly Gln Gly Thr Thr Val Thr Val Ser Ser
    130                 135                 140

Gly Gly Gly Gly Ser Gly Gly Gly Ser Gly Gly Gly Gly Ser Asp
145                 150                 155                 160

Ile Glu Leu Thr Gln Ser Pro Ala Ile Met Ser Ala Ser Pro Gly Glu
                165                 170                 175

Lys Val Thr Met Thr Cys Ser Ala Ser Ser Ser Val Ser Tyr Met His
            180                 185                 190

Trp Tyr Gln Gln Lys Ser Gly Thr Ser Pro Lys Arg Trp Ile Tyr Asp
        195                 200                 205

Thr Ser Lys Leu Ala Ser Gly Val Pro Gly Arg Phe Ser Gly Ser Gly
    210                 215                 220

Ser Gly Asn Ser Tyr Ser Leu Thr Ile Ser Ser Val Glu Ala Glu Asp
225                 230                 235                 240

Asp Ala Thr Tyr Tyr Cys Gln Gln Trp Ser Gly Tyr Pro Leu Thr Phe
                245                 250                 255

Gly Ala Gly Thr Lys Leu Glu Ile Lys Ala Ala Ala Ile Glu Val Met
            260                 265                 270

Tyr Pro Pro Pro Tyr Leu Asp Asn Glu Lys Ser Asn Gly Thr Ile Ile
        275                 280                 285

His Val Lys Gly Lys His Leu Cys Pro Ser Pro Leu Phe Pro Gly Pro
    290                 295                 300

Ser Lys Pro Phe Trp Val Leu Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
```

```
            370                 375                 380
Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 19
<211> LENGTH: 551
<212> TYPE: PRT
<213> ORGANISM: Artificial Sequence
<220> FEATURE:
<223> OTHER INFORMATION: SSscFv-CD28BBZ CAR

<400> SEQUENCE: 19

Met Val Leu Leu Val Thr Ser Leu Leu Leu Cys Glu Leu Pro His Pro
1               5                   10                  15

Ala Phe Leu Leu Ile Pro Asp Ile Gln Gln Val Gln Leu Gln Gln Ser
            20                  25                  30

Gly Pro Glu Leu Glu Lys Pro Gly Ala Ser Val Lys Ile Ser Cys Lys
        35                  40                  45

Ala Ser Gly Tyr Ser Phe Thr Gly Tyr Thr Met Asn Trp Val Lys Gln
50                  55                  60

Ser His Gly Lys Ser Leu Glu Trp Ile Gly Leu Ile Thr Pro Tyr Asn
65                  70                  75                  80

Gly Ala Ser Ser Tyr Asn Gln Lys Phe Arg Gly Lys Ala Thr Leu Thr
                85                  90                  95

Val Asp Lys Ser Ser Ser Thr Ala Tyr Met Asp Leu Leu Ser Leu Thr
            100                 105                 110

Ser Glu Asp Ser Ala Val Tyr Phe Cys Ala Arg Gly Gly Tyr Asp Gly
        115                 120                 125

Arg Gly Phe Asp Tyr Trp Gly Gln Gly Thr Thr Val Thr Val Ser Ser
130                 135                 140

Gly Gly Gly Gly Ser Gly Gly Gly Gly Ser Gly Gly Gly Gly Ser Asp
145                 150                 155                 160

Ile Glu Leu Thr Gln Ser Pro Ala Ile Met Ser Ala Ser Pro Gly Glu
                165                 170                 175

Lys Val Thr Met Thr Cys Ser Ala Ser Ser Ser Val Ser Tyr Met His
            180                 185                 190

Trp Tyr Gln Gln Lys Ser Gly Thr Ser Pro Lys Arg Trp Ile Tyr Asp
        195                 200                 205

Thr Ser Lys Leu Ala Ser Gly Val Pro Gly Arg Phe Ser Gly Ser Gly
            210                 215                 220

Ser Gly Asn Ser Tyr Ser Leu Thr Ile Ser Ser Val Glu Ala Glu Asp
225                 230                 235                 240

Asp Ala Thr Tyr Tyr Cys Gln Gln Trp Ser Gly Tyr Pro Leu Thr Phe
```

245                 250                 255
Gly Ala Gly Thr Lys Leu Glu Ile Lys Ala Ala Phe Val Pro Val
            260                 265                 270

Phe Leu Pro Ala Lys Pro Thr Thr Thr Pro Ala Pro Arg Pro Pro Thr
        275                 280                 285

Pro Ala Pro Thr Ile Ala Ser Gln Pro Leu Ser Leu Arg Pro Glu Ala
    290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Asn His Arg Asn Arg
            340                 345                 350

Ser Lys Arg Ser Arg Leu Leu His Ser Asp Tyr Met Asn Met Thr Pro
        355                 360                 365

Arg Arg Pro Gly Pro Thr Arg Lys His Tyr Gln Pro Tyr Ala Pro Pro
    370                 375                 380

Arg Asp Phe Ala Ala Tyr Arg Ser Arg Phe Ser Val Val Lys Arg Gly
385                 390                 395                 400

Arg Lys Lys Leu Leu Tyr Ile Phe Lys Gln Pro Phe Met Arg Pro Val
                405                 410                 415

Gln Thr Thr Gln Glu Glu Asp Gly Cys Ser Cys Arg Phe Pro Glu Glu
            420                 425                 430

Glu Glu Gly Gly Cys Glu Leu Arg Val Lys Phe Ser Arg Ser Ala Asp
        435                 440                 445

Ala Pro Ala Tyr Gln Gln Gly Gln Asn Gln Leu Tyr Asn Glu Leu Asn
    450                 455                 460

Leu Gly Arg Arg Glu Glu Tyr Asp Val Leu Asp Lys Arg Arg Gly Arg
465                 470                 475                 480

Asp Pro Glu Met Gly Gly Lys Pro Arg Arg Lys Asn Pro Gln Glu Gly
                485                 490                 495

Leu Tyr Asn Glu Leu Gln Lys Asp Lys Met Ala Glu Ala Tyr Ser Glu
            500                 505                 510

Ile Gly Met Lys Gly Glu Arg Arg Arg Gly Lys Gly His Asp Gly Leu
        515                 520                 525

Tyr Gln Gly Leu Ser Thr Ala Thr Lys Asp Thr Tyr Asp Ala Leu His
    530                 535                 540

Met Gln Ala Leu Pro Pro Arg
545                 550

<210> SEQ ID NO 20
<211> LENGTH: 487
<212> TYPE: PRT
<213> ORGANISM: Artificial Sequence
<220> FEATURE:
<223> OTHER INFORMATION: SS1scFv-28Z CAR

<400> SEQUENCE: 20

Met Val Leu Leu Val Thr Ser Leu Leu Leu Cys Glu Leu Pro His Pro
1               5                   10                  15

Ala Phe Leu Leu Ile Pro Asp Ile Gln Gln Val Gln Leu Gln Gln Ser
            20                  25                  30

Gly Pro Glu Leu Glu Lys Pro Gly Ala Ser Val Lys Ile Ser Cys Lys
        35                  40                  45

Ala Ser Gly Tyr Ser Phe Thr Gly Tyr Thr Met Asn Trp Val Lys Gln

```
                50                  55                  60
Ser His Gly Lys Ser Leu Glu Trp Ile Gly Leu Ile Thr Pro Tyr Asn
 65                  70                  75                  80

Gly Ala Ser Ser Tyr Asn Gln Lys Phe Arg Gly Lys Ala Thr Leu Thr
                 85                  90                  95

Val Asp Lys Ser Ser Ser Thr Ala Tyr Met Asp Leu Leu Ser Leu Thr
            100                 105                 110

Ser Glu Asp Ser Ala Val Tyr Phe Cys Ala Arg Gly Gly Tyr Asp Gly
            115                 120                 125

Arg Gly Phe Asp Tyr Trp Gly Gln Gly Thr Thr Val Thr Val Ser Ser
        130                 135                 140

Gly Gly Gly Gly Ser Gly Gly Gly Ser Gly Gly Gly Gly Ser Asp
145                 150                 155                 160

Ile Glu Leu Thr Gln Ser Pro Ala Ile Met Ser Ala Ser Pro Gly Glu
                165                 170                 175

Lys Val Thr Met Thr Cys Ser Ala Ser Ser Ser Val Ser Tyr Met His
            180                 185                 190

Trp Tyr Gln Gln Lys Ser Gly Thr Ser Pro Lys Arg Trp Ile Tyr Asp
        195                 200                 205

Thr Ser Lys Leu Ala Ser Gly Val Pro Gly Arg Phe Ser Gly Ser Gly
    210                 215                 220

Ser Gly Asn Ser Tyr Ser Leu Thr Ile Ser Ser Val Glu Ala Glu Asp
225                 230                 235                 240

Asp Ala Thr Tyr Tyr Cys Gln Gln Trp Ser Lys His Pro Leu Thr Phe
                245                 250                 255

Gly Ala Gly Thr Lys Leu Glu Ile Lys Ala Ala Ala Ile Glu Val Met
            260                 265                 270

Tyr Pro Pro Pro Tyr Leu Asp Asn Glu Lys Ser Asn Gly Thr Ile Ile
        275                 280                 285

His Val Lys Gly Lys His Leu Cys Pro Ser Pro Leu Phe Pro Gly Pro
    290                 295                 300

Ser Lys Pro Phe Trp Val Leu Val Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480
```

```
Met Gln Ala Leu Pro Pro Arg
            485

<210> SEQ ID NO 21
<211> LENGTH: 551
<212> TYPE: PRT
<213> ORGANISM: Artificial Sequence
<220> FEATURE:
<223> OTHER INFORMATION: SS1scFv-28BBZ CAR

<400> SEQUENCE: 21

Met Val Leu Leu Val Thr Ser Leu Leu Leu Cys Glu Leu Pro His Pro
1               5                   10                  15

Ala Phe Leu Leu Ile Pro Asp Ile Gln Gln Val Gln Leu Gln Gln Ser
            20                  25                  30

Gly Pro Glu Leu Glu Lys Pro Gly Ala Ser Val Lys Ile Ser Cys Lys
        35                  40                  45

Ala Ser Gly Tyr Ser Phe Thr Gly Tyr Thr Met Asn Trp Val Lys Gln
    50                  55                  60

Ser His Gly Lys Ser Leu Glu Trp Ile Gly Leu Ile Thr Pro Tyr Asn
65                  70                  75                  80

Gly Ala Ser Ser Tyr Asn Gln Lys Phe Arg Gly Lys Ala Thr Leu Thr
                85                  90                  95

Val Asp Lys Ser Ser Ser Thr Ala Tyr Met Asp Leu Leu Ser Leu Thr
            100                 105                 110

Ser Glu Asp Ser Ala Val Tyr Phe Cys Ala Arg Gly Gly Tyr Asp Gly
        115                 120                 125

Arg Gly Phe Asp Tyr Trp Gly Gln Gly Thr Thr Val Thr Val Ser Ser
    130                 135                 140

Gly Gly Gly Gly Ser Gly Gly Gly Ser Gly Gly Gly Ser Asp
145                 150                 155                 160

Ile Glu Leu Thr Gln Ser Pro Ala Ile Met Ser Ala Ser Pro Gly Glu
                165                 170                 175

Lys Val Thr Met Thr Cys Ser Ala Ser Ser Ser Val Ser Tyr Met His
            180                 185                 190

Trp Tyr Gln Gln Lys Ser Gly Thr Ser Pro Lys Arg Trp Ile Tyr Asp
        195                 200                 205

Thr Ser Lys Leu Ala Ser Gly Val Pro Gly Arg Phe Ser Gly Ser Gly
    210                 215                 220

Ser Gly Asn Ser Tyr Ser Leu Thr Ile Ser Ser Val Glu Ala Glu Asp
225                 230                 235                 240

Asp Ala Thr Tyr Tyr Cys Gln Gln Trp Ser Lys His Pro Leu Thr Phe
                245                 250                 255

Gly Ala Gly Thr Lys Leu Glu Ile Lys Ala Ala Ala Phe Val Pro Val
            260                 265                 270

Phe Leu Pro Ala Lys Pro Thr Thr Thr Pro Ala Pro Arg Pro Pro Thr
        275                 280                 285

Pro Ala Pro Thr Ile Ala Ser Gln Pro Leu Ser Leu Arg Pro Glu Ala
    290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Asn His Arg Asn Arg
            340                 345                 350
```

```
Ser Lys Arg Ser Arg Leu Leu His Ser Asp Tyr Met Asn Met Thr Pro
        355                 360                 365

Arg Arg Pro Gly Pro Thr Arg Lys His Tyr Gln Pro Tyr Ala Pro Pro
370                 375                 380

Arg Asp Phe Ala Ala Tyr Arg Ser Arg Phe Ser Val Val Lys Arg Gly
385                 390                 395                 400

Arg Lys Lys Leu Leu Tyr Ile Phe Lys Gln Pro Phe Met Arg Pro Val
                405                 410                 415

Gln Thr Thr Gln Glu Glu Asp Gly Cys Ser Cys Arg Phe Pro Glu Glu
            420                 425                 430

Glu Glu Gly Gly Cys Glu Leu Arg Val Lys Phe Ser Arg Ser Ala Asp
            435                 440                 445

Ala Pro Ala Tyr Gln Gln Gly Gln Asn Gln Leu Tyr Asn Glu Leu Asn
        450                 455                 460

Leu Gly Arg Arg Glu Glu Tyr Asp Val Leu Asp Lys Arg Arg Gly Arg
465                 470                 475                 480

Asp Pro Glu Met Gly Gly Lys Pro Arg Arg Lys Asn Pro Gln Glu Gly
                485                 490                 495

Leu Tyr Asn Glu Leu Gln Lys Asp Lys Met Ala Glu Ala Tyr Ser Glu
            500                 505                 510

Ile Gly Met Lys Gly Glu Arg Arg Arg Gly Lys Gly His Asp Gly Leu
        515                 520                 525

Tyr Gln Gly Leu Ser Thr Ala Thr Lys Asp Thr Tyr Asp Ala Leu His
        530                 535                 540

Met Gln Ala Leu Pro Pro Arg
545                 550

<210> SEQ ID NO 22
<211> LENGTH: 490
<212> TYPE: PRT
<213> ORGANISM: Artificial Sequence
<220> FEATURE:
<223> OTHER INFORMATION: HN1scFv-28Z

<400> SEQUENCE: 22

Met Val Leu Leu Val Thr Ser Leu Leu Leu Cys Glu Leu Pro His Pro
1               5                   10                  15

Ala Phe Leu Leu Ile Pro Asp Ile Gln Ala Gln Val Gln Leu Val Gln
            20                  25                  30

Ser Gly Ala Glu Val Lys Arg Pro Gly Ala Ser Val Gln Val Ser Cys
        35                  40                  45

Arg Ala Ser Gly Tyr Ser Ile Asn Thr Tyr Tyr Met Gln Trp Val Arg
    50                  55                  60

Gln Ala Pro Gly Ala Gly Leu Glu Trp Met Gly Val Ile Asn Pro Ser
65                  70                  75                  80

Gly Val Thr Ser Tyr Ala Gln Lys Phe Gln Gly Arg Val Thr Leu Thr
                85                  90                  95

Asn Asp Thr Ser Thr Asn Thr Val Tyr Met Gln Leu Asn Ser Leu Thr
            100                 105                 110

Ser Ala Asp Thr Ala Val Tyr Tyr Cys Ala Arg Trp Ala Leu Trp Gly
        115                 120                 125

Asp Phe Gly Met Asp Val Trp Gly Lys Gly Thr Leu Val Thr Val Ser
    130                 135                 140

Ser Gly Gly Gly Gly Ser Gly Gly Gly Ser Gly Gly Gly Gly Ser
145                 150                 155                 160
```

```
Asp Ile Gln Met Thr Gln Ser Pro Ser Thr Leu Ser Ala Ser Ile Gly
            165                 170                 175

Asp Arg Val Thr Ile Thr Cys Arg Ala Ser Glu Gly Ile Tyr His Trp
        180                 185                 190

Leu Ala Trp Tyr Gln Gln Lys Pro Gly Lys Ala Pro Lys Leu Leu Ile
            195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala Ile
            260                 265                 270

Glu Val Met Tyr Pro Pro Pro Tyr Leu Asp Asn Glu Lys Ser Asn Gly
        275                 280                 285

Thr Ile Ile His Val Lys Gly Lys His Leu Cys Pro Ser Pro Leu Phe
            290                 295                 300

Pro Gly Pro Ser Lys Pro Phe Trp Val Leu Val Val Val Gly Gly Val
305                 310                 315                 320

Leu Ala Cys Tyr Ser Leu Leu Val Thr Val Ala Phe Ile Ile Phe Trp
                325                 330                 335

Val Arg Ser Lys Arg Ser Arg Leu Leu His Ser Asp Tyr Met Asn Met
            340                 345                 350

Thr Pro Arg Arg Pro Gly Pro Thr Arg Lys His Tyr Gln Pro Tyr Ala
        355                 360                 365

Pro Pro Arg Asp Phe Ala Ala Tyr Arg Ser Arg Val Lys Phe Ser Arg
            370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 23
<211> LENGTH: 554
<212> TYPE: PRT
<213> ORGANISM: Artificial Sequence
<220> FEATURE:
<223> OTHER INFORMATION: HN1scFv-28BBZ CAR

<400> SEQUENCE: 23

Met Val Leu Leu Val Thr Ser Leu Leu Leu Cys Glu Leu Pro His Pro
1               5                   10                  15

Ala Phe Leu Leu Ile Pro Asp Ile Gln Ala Gln Val Gln Leu Val Gln
            20                  25                  30
```

```
Ser Gly Ala Glu Val Lys Arg Pro Gly Ala Ser Val Gln Val Ser Cys
        35                  40                  45

Arg Ala Ser Gly Tyr Ser Ile Asn Thr Tyr Tyr Met Gln Trp Val Arg
 50                  55                  60

Gln Ala Pro Gly Ala Gly Leu Glu Trp Met Gly Val Ile Asn Pro Ser
 65                  70                  75                  80

Gly Val Thr Ser Tyr Ala Gln Lys Phe Gln Gly Arg Val Thr Leu Thr
                 85                  90                  95

Asn Asp Thr Ser Thr Asn Thr Val Tyr Met Gln Leu Asn Ser Leu Thr
                100                 105                 110

Ser Ala Asp Thr Ala Val Tyr Tyr Cys Ala Arg Trp Ala Leu Trp Gly
                115                 120                 125

Asp Phe Gly Met Asp Val Trp Gly Lys Gly Thr Leu Val Thr Val Ser
130                 135                 140

Ser Gly Gly Gly Gly Ser Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
                180                 185                 190

Leu Ala Trp Tyr Gln Gln Lys Pro Gly Lys Ala Pro Lys Leu Leu Ile
                195                 200                 205

Tyr Lys Ala Ser Ser Leu Ala Ser Gly Ala Pro Ser Arg Phe Ser Gly
210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala Phe
                260                 265                 270

Val Pro Val Phe Leu Pro Ala Lys Pro Thr Thr Thr Pro Ala Pro Arg
                275                 280                 285

Pro Pro Thr Pro Ala Pro Thr Ile Ala Ser Gln Pro Leu Ser Leu Arg
                290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Asn His
                340                 345                 350

Arg Asn Arg Ser Lys Arg Ser Arg Leu Leu His Ser Asp Tyr Met Asn
                355                 360                 365

Met Thr Pro Arg Arg Pro Gly Pro Thr Arg Lys His Tyr Gln Pro Tyr
370                 375                 380

Ala Pro Pro Arg Asp Phe Ala Ala Tyr Arg Ser Arg Phe Ser Val Val
385                 390                 395                 400

Lys Arg Gly Arg Lys Lys Leu Leu Tyr Ile Phe Lys Gln Pro Phe Met
                405                 410                 415

Arg Pro Val Gln Thr Thr Gln Glu Glu Asp Gly Cys Ser Cys Arg Phe
                420                 425                 430

Pro Glu Glu Glu Glu Gly Gly Cys Glu Leu Arg Val Lys Phe Ser Arg
                435                 440                 445
```

```
Ser Ala Asp Ala Pro Ala Tyr Gln Gln Gly Gln Asn Gln Leu Tyr Asn
    450                 455                 460

Glu Leu Asn Leu Gly Arg Arg Glu Glu Tyr Asp Val Leu Asp Lys Arg
465                 470                 475                 480

Arg Gly Arg Asp Pro Glu Met Gly Gly Lys Pro Arg Arg Lys Asn Pro
                485                 490                 495

Gln Glu Gly Leu Tyr Asn Glu Leu Gln Lys Asp Lys Met Ala Glu Ala
            500                 505                 510

Tyr Ser Glu Ile Gly Met Lys Gly Glu Arg Arg Arg Gly Lys Gly His
        515                 520                 525

Asp Gly Leu Tyr Gln Gly Leu Ser Thr Ala Thr Lys Asp Thr Tyr Asp
530                 535                 540

Ala Leu His Met Gln Ala Leu Pro Pro Arg
545                 550

<210> SEQ ID NO 24
<211> LENGTH: 795
<212> TYPE: DNA
<213> ORGANISM: Artificial Sequence
<220> FEATURE:
<223> OTHER INFORMATION: Codon optimized SS scFv

<400> SEQUENCE: 24
atggttctgc tggtcaccag cctgctgctg tgcgaactgc ccacccgc ctttctgctg      60 atccccgaca tccagcaggt ccagctccag cagtctggcc tgaactgga aaacctggg    120 gctagcgtga aaatctcctg taaggcatcc ggatactcat tcaccggcta caccatgaat   180
tgggtcaaac agagccacgg caaatcactc gagtggatcg gactcatcac tccctacaat   240
ggcgcctctt catacaatca gaaattccgg ggcaaagcaa cactcactgt ggacaaatcc   300
tcttccaccg cctacatgga tctgctgtct ctcacctctg aggactccgc tgtgtacttt   360
tgtgctcggg gggatacga cggacggggc ttcgattact gggggcaggg aacaactgtg   420
actgtgtcta gtggaggggg cggatctggg ggaggcggat ccggcggagg aggctccgat   480
attgaactca cccagtctcc cgctatcatg tctgcttcac ctggcgagaa agtgactatg   540
acctgttctg cctcatcttc cgtgtcctac atgcactggt accagcagaa atctggcaca   600
tcccctaaac gctggatcta cgacacctct aaactggcat ctggcgtgcc tgccgcttc   660 tctggctccg gctccggcaa ttcttactct ctcacaatct cctctgtgga ggctgaggat   720
gatgccacat actactgtca gcagtggagt ggctacccac tcacatttgg cgctggcact   780
aaactcgaaa tcaaa                                                  795

<210> SEQ ID NO 25
<211> LENGTH: 795
<212> TYPE: DNA
<213> ORGANISM: Artificial Sequence
<220> FEATURE:
<223> OTHER INFORMATION: Codon optimized SS1 scFv

<400> SEQUENCE: 25
atggttctgc tggtgacatc tctcctgctc tgtgaactgc tcatcccgc ttttctgctc      60 attcccgaca ttcagcaggt ccagctccag cagtctggcc tgaactcga aaacctggc    120 gctagcgtga aaatttcctg taaagcctcc ggctactctt ttactggcta cacaatgaat   180
tgggtgaaac agtctcacgg caaatccctc gaatggatcg gactcatcac acctacaat   240 ggcgcctctt cctacaacca gaaattccgg ggcaaggcaa cactcactgt ggacaaatca   300
```

| | |
|---|---|
| tcctctaccg cctacatgga tctgctctcc ctcacatctg aggactccgc tgtctacttt | 360 |
| tgtgcccgag aggatacga cggacgagga ttcgattact ggggacaggg aacaactgtg | 420 |
| accgtgtcta gtggcggcgg agggagtgga ggcggaggat cttctggcgg gggatccgat | 480 |
| attgaactca cacagtctcc cgctatcatg tctgcttctc ccggcgagaa agtgactatg | 540 |
| acttgctctg cttcctcttc tgtgtcctac atgcactggt accagcagaa atctggcaca | 600 |
| tcccctaaac ggtggatcta cgatactagc aaactggcat ccggcgtgcc tgggcgattc | 660 |
| tctggctctg gctctggcaa ctcttactct ctcacaatct catctgtcga ggctgaggac | 720 |
| gatgccacat actactgtca gcagtggtct aaacacccac tcacattcgg cgctggcact | 780 |
| aaactggaaa taaaa | 795 |

<210> SEQ ID NO 26
<211> LENGTH: 804
<212> TYPE: DNA
<213> ORGANISM: Artificial Sequence
<220> FEATURE:
<223> OTHER INFORMATION: Codon optimized HN1 scFv

<400> SEQUENCE: 26

| | |
|---|---|
| atggttctgc tggtgacatc tctcctgctc tgtgaactgc ctcatcccgc ttttctgctc | 60 |
| attcccgaca ttcaggctca agtccaactg gtccaaagtg gtgctgaagt caaacgcccg | 120 |
| ggtgcctccg tccaagtctc ctgccgtgcc tctggctact cgattaacac ctattacatg | 180 |
| cagtgggtcc gtcaagcacc gggtgcaggt ctggaatgga tgggtgtcat caatccgtcc | 240 |
| ggcgtgacct catatgcgca gaaatttcaa gtcgcgtta ccctgacgaa cgataccagc | 300 |
| acgaataccg tctacatgca gctgaactct ctgacgagtg cagacaccgc ggtgtattac | 360 |
| tgcgcacgtt gggcactgtg ggcgatttc ggcatggatg tttggggcaa aggtacgctg | 420 |
| gtgaccgtta gctctggtgg tggtggttct ggtggtggtg gtagtggcgg tggcggttct | 480 |
| gatattcaga tgacgcaaag cccgtctacc ctgagtgcct ccattggtga ccgtgttacg | 540 |
| atcacctgtc gcgcatccga aggcatctat cattggctgg cttggtacca gcaaaaaccg | 600 |
| ggtaaagcgc cgaaactgct gatctataaa gcaagttccc tggcatcggg tgctccgagc | 660 |
| cgcttttcag gttcgggtag cggcaccgat ttcacgctga ccatctcatc gctgcagccg | 720 |
| gacgatttcg ctacctacta ctgccaacaa tactcaaact acccgctgac cttcggtgga | 780 |
| gggaccaagc tggagatcaa acgt | 804 |

<210> SEQ ID NO 27
<211> LENGTH: 1464
<212> TYPE: DNA
<213> ORGANISM: Artificial Sequence
<220> FEATURE:
<223> OTHER INFORMATION: Codon optimized SSscFv-CD28Z CAR

<400> SEQUENCE: 27

| | |
|---|---|
| atggttctgc tggtcaccag cctgctgctg tgcgaactgc cccaccccgc ctttctgctg | 60 |
| atccccgaca tccagcaggt ccagctccag cagtctggcc ctgaactgga aaaacctggg | 120 |
| gctagcgtga aaatctcctg taaggcatcc ggatactcat tcaccggcta caccatgaat | 180 |
| tgggtcaaac agagccacgg caaatcactc gagtggatcg gactcatcac tccctacaat | 240 |
| ggcgcctctt catacaatca gaaattccgg ggcaaagcaa cactcactgt ggacaaatcc | 300 |
| tcttccaccg cctacatgga tctgctgtct ctcacctctg aggactccgc tgtgtacttt | 360 |
| tgtgctcggg ggggatacga cggacggggc ttcgattact gggggcaggg aacaactgtg | 420 |

```
actgtgtcta gtggaggggg cggatctggg ggaggcggat ccggcggagg aggctccgat      480
attgaactca cccagtctcc cgctatcatg tctgcttcac ctggcgagaa agtgactatg      540
acctgttctg cctcatcttc cgtgtcctac atgcactggt accagcagaa atctggcaca      600
tcccctaaac gctggatcta cgacacctct aaactggcat ctggcgtgcc tggccgcttc      660
tctggctccg gctccggcaa ttcttactct ctcacaatct cctctgtgga ggctgaggat      720
gatgccacat actactgtca gcagtggagt ggctacccac tcacatttgg cgctggcact      780
aaactcgaaa tcaaagcggc cgcaattgaa gttatgtatc ctcctcctta cctagacaat      840
gagaagagca tggaaccat  tatccatgtg aaagggaaac cctttgtcc  aagtccccta      900 tttcccggac cttctaagcc cttttgggtg ctggtggtgg ttggtggagt cctggcttgc      960
tatagcttgc tagtaacagt ggcctttatt attttctggg tgaggagtaa gaggagcagg     1020
ctcctgcaca gtgactacat gaacatgact ccccgccgcc ccgggcccac ccgcaagcat     1080
taccagccct atgccccacc acgcgacttc gcagcctatc gctccagagt gaagttcagc     1140
aggagcgcag acgccccgc  gtaccagcag ggccagaacc agctctataa cgagctcaat     1200
ctaggacgaa gagaggagta cgatgttttg gacaagagac gtggccggga ccctgagatg     1260
gggggaaagc cgagaaggaa gaaccctcag gaaggcctgt acaatgaact gcagaaagat     1320
aagatggcgg aggcctacag tgagattggg atgaaaggcg agcgccggag gggcaagggg     1380
cacgatggcc tttaccaggg tctcagtaca gccaccaagg acacctacga cgcccttcac     1440
atgcaggccc tgccccctcg ctaa                                            1464

<210> SEQ ID NO 28
<211> LENGTH: 1656
<212> TYPE: DNA
<213> ORGANISM: Artificial Sequence
<220> FEATURE:
<223> OTHER INFORMATION: Codon optimized  SSscFv-CD28BBZ CAR

<400> SEQUENCE: 28
atggttctgc tggtcaccag cctgctgctg tgcgaactgc cccacccgc  ctttctgctg       60 atccccgaca tccagcaggt ccagctccag cagtctggcc tgaactgga  aaaacctggg      120 gctagcgtga aaatctcctg taaggcatcc ggatactcat tcaccggcta caccatgaat      180
tgggtcaaac agagccacgg caaatcactc gagtggatcg gactcatcac tccctacaat      240
ggcgcctctt catacaatca gaaattccgg ggcaaagcaa cactcactgt ggacaaatcc      300
tcttccaccg cctacatgga tctgctgtct ctcacctctg aggactccgc tgtgtacttt      360
tgtgctcggg ggggatacga cggacggggc ttcgattact gggggcaggg aacaactgtg      420
actgtgtcta gtggaggggg cggatctggg ggaggcggat ccggcggagg aggctccgat      480
attgaactca cccagtctcc cgctatcatg tctgcttcac ctggcgagaa agtgactatg      540
acctgttctg cctcatcttc cgtgtcctac atgcactggt accagcagaa atctggcaca      600
tcccctaaac gctggatcta cgacacctct aaactggcat ctggcgtgcc tggccgcttc      660
tctggctccg gctccggcaa ttcttactct ctcacaatct cctctgtgga ggctgaggat      720
gatgccacat actactgtca gcagtggagt ggctacccac tcacatttgg cgctggcact      780
aaactcgaaa tcaaagcggc cgcattcgtg ccggtcttcc tgccagcgaa gcccaccacg      840
acgccagcgc cgcgaccacc aacaccggcg cccaccatcg cgtcgcagcc cctgtccctg      900
cgcccagagg cgtgccggcc agcggcgggg ggcgcagtgc acacgagggg gctggacttc      960
```

| | |
|---|---|
| gcctgtgata tctacatctg gcgcccttg gccgggactt gtggggtcct tctcctgtca | 1020 |
| ctggttatca ccctttactg caaccacagg aacaggagta agaggagcag gctcctgcac | 1080 |
| agtgactaca tgaacatgac tccccgccgc cccgggccca cccgcaagca ttaccagccc | 1140 |
| tatgccccac cacgcgactt cgcagcctat cgctcccgtt tctctgttgt taaacggggc | 1200 |
| agaaagaaac tcctgtatat attcaaacaa ccatttatga gaccagtaca aactactcaa | 1260 |
| gaggaagatg gctgtagctg ccgatttcca gaagaagaag aaggaggatg tgaactgaga | 1320 |
| gtgaagttca gcaggagcgc agacgccccc gcgtaccagc agggccagaa ccagctctat | 1380 |
| aacgagctca atctaggacg aagagaggag tacgatgttt tggacaagag acgtggccgg | 1440 |
| gaccctgaga tggggggaaa gccgagaagg aagaaccctc aggaaggcct gtacaatgaa | 1500 |
| ctgcagaaag ataagatggc ggaggcctac agtgagattg gatgaaaagg cgagcgccgg | 1560 |
| aggggcaagg ggcacgatgg cctttaccag ggtctcagta cagccaccaa ggacacctac | 1620 |
| gacgcccttc acatgcaggc cctgccccct cgctaa | 1656 |

<210> SEQ ID NO 29
<211> LENGTH: 1464
<212> TYPE: DNA
<213> ORGANISM: Artificial Sequence
<220> FEATURE:
<223> OTHER INFORMATION: Codon optimized SS1scFv-28Z CAR

<400> SEQUENCE: 29

| | |
|---|---|
| atggttctgc tggtgacatc tctcctgctc tgtgaactgc ctcatcccgc ttttctgctc | 60 |
| attcccgaca ttcagcaggt ccagctccag cagtctggcc ctgaactcga aaaacctggc | 120 |
| gctagcgtga aaattcctg taaagcctcc ggctactctt ttactggcta cacaatgaat | 180 |
| tgggtgaaac agtctcacgg caaatccctc gaatggatcg gactcatcac accctacaat | 240 |
| ggcgcctctt cctacaacca gaaattccgg ggcaaggcaa cactcactgt ggacaaatca | 300 |
| tcctctaccg cctacatgga tctgctctcc ctcacatctg aggactccgc tgtctacttt | 360 |
| tgtgcccgag aggatacga cggacgagga ttcgattact ggggacaggg aacaactgtg | 420 |
| accgtgtcta gtggcggcgg agggagtgga ggcggaggat cttctggcgg gggatccgat | 480 |
| attgaactca cacagtctcc cgctatcatg tctgcttctc ccggcgagaa agtgactatg | 540 |
| acttgctctg cttcctcttc tgtgtcctac atgcactggt accagcagaa atctggcaca | 600 |
| tcccctaaac ggtggatcta cgatactagc aaactggcat ccggcgtgcc tgggcgattc | 660 |
| tctggctctg gctctggcaa ctcttactct ctcacaatct catctgtcga ggctgaggac | 720 |
| gatgccacat actactgtca gcagtggtct aaacacccac tcacattcgg cgctggcact | 780 |
| aaactgaaaa taaagcggc cgcaattgaa gttatgtatc ctcctcctta cctagacaat | 840 |
| gagaagagca atggaaccat tatccatgtg aaagggaaac cctttgtcc aagtccccta | 900 |
| tttcccggac ttctaagcc ttttggggtg ctggtggtgg ttggtggagt cctggcttgc | 960 |
| tatagcttgc tagtaacagt ggcctttatt attttctggg tgaggagtaa gaggagcagg | 1020 |
| ctcctgcaca gtgactacat gaacatgact ccccgccgcc ccgggcccac ccgcaagcat | 1080 |
| taccagccct atgccccacc acgcgacttc gcagcctatc gctccagagt gaagttcagc | 1140 |
| aggagcgcag acgccccgc gtaccagcag ggccagaacc agctctataa cgagctcaat | 1200 |
| ctaggacgaa gagaggagta cgatgttttg gacaagagac gtggccggga ccctgagatg | 1260 |
| gggggaaagc cgagaaggaa gaaccctcag gaaggcctgt acaatgaact gcagaaagat | 1320 |
| aagatggcgg aggcctacag tgagattggg atgaaaggcg agcgccggag gggcaagggg | 1380 |

-continued

```
cacgatggcc tttaccaggg tctcagtaca gccaccaagg acacctacga cgcccttcac    1440
atgcaggccc tgccccctcg ctaa                                          1464

<210> SEQ ID NO 30
<211> LENGTH: 1656
<212> TYPE: DNA
<213> ORGANISM: Artificial Sequence
<220> FEATURE:
<223> OTHER INFORMATION: Codon optimized  SS1scFv-28BBZ CAR

<400> SEQUENCE: 30
atggttctgc tggtgacatc tctcctgctc tgtgaactgc ctcatcccgc ttttctgctc     60
attcccgaca ttcagcaggt ccagctccag cagtctggcc ctgaactcga aaacctggc    120 gctagcgtga aatttcctg taaagcctcc ggctactctt ttactggcta cacaatgaat    180
tgggtgaaac agtctcacgg caaatccctc gaatggatcg actcatcac accctacaat    240 ggcgcctctt cctacaacca gaaattccgg ggcaaggcaa cactcactgt ggacaaatca    300
tcctctaccg cctacatgga tctgctctcc ctcacatctg aggactccgc tgtctacttt    360
tgtgcccgag aggatacga cggacgagga ttcgattact ggggacaggg aacaactgtg    420
accgtgtcta gtggcggcgg agggagtgga ggcggaggat cttctggcgg gggatccgat    480
attgaactca cacagtctcc cgctatcatg tctgcttctc ccggcgagaa agtgactatg    540
acttgctctg cttcctcttc tgtgtcctac atgcactggt accagcagaa atctggcaca    600
tcccctaaac ggtggatcta cgatactagc aaactggcat ccggcgtgcc tgggcgattc    660
tctggctctg gctctggcaa ctcttactct ctcacaatct catctgtcga ggctgaggac    720
gatgccacat actactgtca gcagtggtct aaacacccac tcacattcgg cgctggcact    780
aaactggaaa taaaagcggc cgcattcgtg ccggtcttcc tgccagcgaa gcccaccacg    840
acgccagcgc cgcgaccacc aacaccggcg cccaccatcg cgtcgcagcc cctgtccctg    900
cgcccagagg cgtgccggcc agcggcgggg ggcgcagtgc acacgagggg gctggacttc    960
gcctgtgata tctacatctg gcgcccttg gccgggactt gtggggtcct tctcctgtca   1020
ctggttatca ccctttactg caaccacagg aacaggagta gaggagcag gctcctgcac   1080 agtgactaca tgaacatgac tccccgccgc cccgggccca cccgcaagca ttaccagccc   1140
tatgccccac cacgcgactt cgcagcctat cgctcccgtt tctctgttgt aaacggggc   1200 agaaagaagc tcctgtatat attcaaacaa ccatttatga ccagtacaa actactcaa    1260 gaggaagatg gctgtagctg ccgatttcca agaagaagaa ggaggatg tgaactgaga   1320 gtgaagttca gcaggagcgc agacgccccc cgcgtaccag agggccagaa ccagctctat   1380
aacgagctca atctaggacg aagagaggag tacgatgttt tggacaagag acgtggccgg   1440
gaccctgaga tggggggaaa gccgagaagg aagaaccctc aggaaggcct gtacaatgaa   1500
ctgcagaaag ataagatggc ggaggcctac agtgagattg gatgaaaagg cgagcgccgg   1560
aggggcaagg ggcacgatgg cctttaccag gtctcagta cagccaccaa ggacacctac   1620 gacgccttc acatgcaggc cctgccccct cgctaa                             1656

<210> SEQ ID NO 31
<211> LENGTH: 1473
<212> TYPE: DNA
<213> ORGANISM: Artificial Sequence
<220> FEATURE:
<223> OTHER INFORMATION: Codon optimized  HN1scFv-28Z
```

<400> SEQUENCE: 31

```
atggttctgc tggtgacatc tctcctgctc tgtgaactgc ctcatcccgc ttttctgctc      60
attcccgaca ttcaggctca gtccaactg gtccaaagtg gtgctgaagt caaacgcccg     120
ggtgcctccg tccaagtctc ctgccgtgcc tctggctact cgattaacac ctattacatg    180
cagtgggtcc gtcaagcacc gggtgcaggt ctggaatgga tgggtgtcat caatccgtcc    240
ggcgtgacct catatgcgca gaaatttcaa ggtcgcgtta ccctgacgaa cgataccagc    300
acgaataccg tctacatgca gctgaactct ctgacgagtg cagacaccgc ggtgtattac    360
tgcgcacgtt gggcactgtg gggcgatttc ggcatggatg tttggggcaa aggtacgctg    420
gtgaccgtta gctctggtgg tggtggttct ggtggtggtg gtagtggcgg tggcggttct    480
gatattcaga tgacgcaaag cccgtctacc ctgagtgcct ccattggtga ccgtgttacg    540
atcacctgtc gcgcatccga aggcatctat cattggctgg cttggtacca gcaaaaaccg    600
ggtaaagcgc cgaaactgct gatctataaa gcaagttccc tggcatcggg tgctccgagc    660
cgcttttcag gttcgggtag cggcaccgat ttcacgctga ccatctcatc gctgcagccg    720
gacgatttcg ctacctacta ctgccaacaa tactcaaact accgctgac cttcggtgga    780
gggaccaagc tggagatcaa acgtgcggcc gcaattgaag ttatgtatcc tcctccttac    840
ctagacaatg agaagagcaa tggaaccatt atccatgtga agggaaaca cctttgtcca    900
agtccctat ttcccggacc ttctaagccc ttttgggtgc tggtggtggt tggtggagtc    960
ctggcttgct atagcttgct agtaacagtg gcctttatta ttttctgggt gaggagtaag   1020
aggagcaggc tcctgcacag tgactacatg aacatgactc cccgccgccc cgggcccacc   1080
cgcaagcatt accagcccta tgccccacca cgcgacttcg cagcctatcg ctccagagtg   1140
aagttcagca ggagcgcaga cgcccccgcg taccagcagg gccagaacca gctctataac   1200
gagctcaatc taggacgaag agaggagtac gatgttttgg acaagagacg tggccgggac   1260
cctgagatgg ggggaaagcc gagaaggaag aaccctcagg aaggcctgta caatgaactg   1320
cagaaagata agatggcgga ggcctacagt gagattggga tgaaaggcga gcgccggagg   1380
ggcaaggggc acgatggcct ttaccagggt ctcagtacag ccaccaagga cacctacgac   1440
gcccttcaca tgcaggccct gccccctcgc taa                                1473
```

<210> SEQ ID NO 32
<211> LENGTH: 1665
<212> TYPE: DNA
<213> ORGANISM: Artificial Sequence
<220> FEATURE:
<223> OTHER INFORMATION: Codon optimized HN1scFv-28BBZ CAR

<400> SEQUENCE: 32

```
atggttctgc tggtgacatc tctcctgctc tgtgaactgc ctcatcccgc ttttctgctc      60
attcccgaca ttcaggctca gtccaactg gtccaaagtg gtgctgaagt caaacgcccg     120
ggtgcctccg tccaagtctc ctgccgtgcc tctggctact cgattaacac ctattacatg    180
cagtgggtcc gtcaagcacc gggtgcaggt ctggaatgga tgggtgtcat caatccgtcc    240
ggcgtgacct catatgcgca gaaatttcaa ggtcgcgtta ccctgacgaa cgataccagc    300
acgaataccg tctacatgca gctgaactct ctgacgagtg cagacaccgc ggtgtattac    360
tgcgcacgtt gggcactgtg gggcgatttc ggcatggatg tttggggcaa aggtacgctg    420
gtgaccgtta gctctggtgg tggtggttct ggtggtggtg gtagtggcgg tggcggttct    480
gatattcaga tgacgcaaag cccgtctacc ctgagtgcct ccattggtga ccgtgttacg    540
```

```
atcacctgtc gcgcatccga aggcatctat cattggctgg cttggtacca gcaaaaaccg    600
ggtaaagcgc cgaaactgct gatctataaa gcaagttccc tggcatcggg tgctccgagc    660
cgcttttcag gttcgggtag cggcaccgat ttcacgctga ccatctcatc gctgcagccg    720
gacgatttcg ctacctacta ctgccaacaa tactcaaact acccgctgac cttcggtgga    780
gggaccaagc tggagatcaa acgtgcggcc gcattcgtgc cggtcttcct gccagcgaag    840
cccaccacga cgccagcgcc gcgaccacca acaccggcgc ccaccatcgc gtcgcagccc    900
ctgtccctgc gcccagaggc gtgccggcca gcggcggggg gcgcagtgca cacgaggggg    960
ctggacttcg cctgtgatat ctacatctgg gcgcccttgg ccgggacttg tggggtcctt   1020
ctcctgtcac tggttatcac cctttactgc aaccacagga acaggagtaa gaggagcagg   1080
ctcctgcaca gtgactacat gaacatgact ccccgccgcc ccgggcccac ccgcaagcat   1140
taccagccct atgccccacc acgcgacttc gcagcctatc gctcccgttt ctctgttgtt   1200
aaacggggca gaaagaagct cctgtatata ttcaaacaac catttatgag accagtacaa   1260
actactcaag aggaagatgg ctgtagctgc cgatttccag aagaagaaga aggaggatgt   1320
gaactgagag tgaagttcag caggagcgca gacgcccccg cgtaccagca gggccagaac   1380
cagctctata acgagctcaa tctaggacga agagaggagt acgatgtttt ggacaagaga   1440
cgtggccggg accctgagat gggggggaaag ccgagaagga agaaccctca ggaaggcctg   1500
tacaatgaac tgcagaaaga taagatggcg gaggcctaca gtgagattgg gatgaaaggc   1560
gagcgccgga ggggcaaggg gcacgatggc ctttaccagg gtctcagtac agccaccaag   1620
gacacctacg acgcccttca catgcaggcc ctgccccctc gctaa                  1665
```

ANTI-MESOTHELIN CHIMERIC ANTIGEN RECEPTORS

CROSS-REFERENCE TO A RELATED APPLICATION

This patent application is the U.S. National Phase of International Patent Application No. PCT/US2013/028980, filed Mar. 5, 2013, which claims the benefit of U.S. Provisional Patent Application No. 61/614,612, filed Mar. 23, 2012, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 62,417 Byte ASCII (Text) file named "718522ST25.TXT" dated Feb. 8, 2013 Aug. 26, 2014.

BACKGROUND OF THE INVENTION

Cancer is a public health concern. Despite advances in treatments such as chemotherapy, the prognosis for many cancers may be poor. For example, in the United States, despite therapy, an estimated 15,000 women die of ovarian cancer each year. Accordingly, there exists an unmet need for additional treatments for cancer.

BRIEF SUMMARY OF THE INVENTION

The invention provides a chimeric antigen receptor (CAR) comprising (a) an antigen binding domain of HN1 or SS, a transmembrane domain, and an intracellular T cell signaling domain, or (b) an antigen binding domain of SS1, a transmembrane domain, an intracellular T cell signaling domain, and a granulocyte-macrophage colony-stimulating factor (GM-CSF) receptor 2 leader.

Further embodiments of the invention provide related nucleic acids, recombinant expression vectors, host cells, populations of cells, antibodies, or antigen binding portions thereof, and pharmaceutical compositions relating to the CARs of the invention.

Additional embodiments of the invention provide methods of detecting the presence of cancer and methods of treating or preventing cancer in a mammal.

BRIEF DESCRIPTION OF THE SEVERAL VIEWS OF THE DRAWING(S)

FIG. 1 is a graph showing interferon (IFN)-γ secretion (pg/ml) by peripheral blood lymphocytes (PBL) from each of three human donors (Patient (Pt.) 1, Pt. 2, and Pt. 3) who were untransduced (UT) or transduced with codon-optimized SS1scFv-CD28Z CAR (SEQ ID NO: 29) (D6 or D8) or codon-optimized SSscFv-CD28Z (SEQ ID NO: 27) (C2 or G8), upon co-culture with target tumor cell lines A431-H9 (dotted bars), A431 (horizontal striped bars), Panc10.05 (cross-hatched bars), or OVCAR5 (black bars). FIG. 1 shows the function of CAR-transduced PBL following initial stimulation with OKT3 during transduction.

Figure 2:
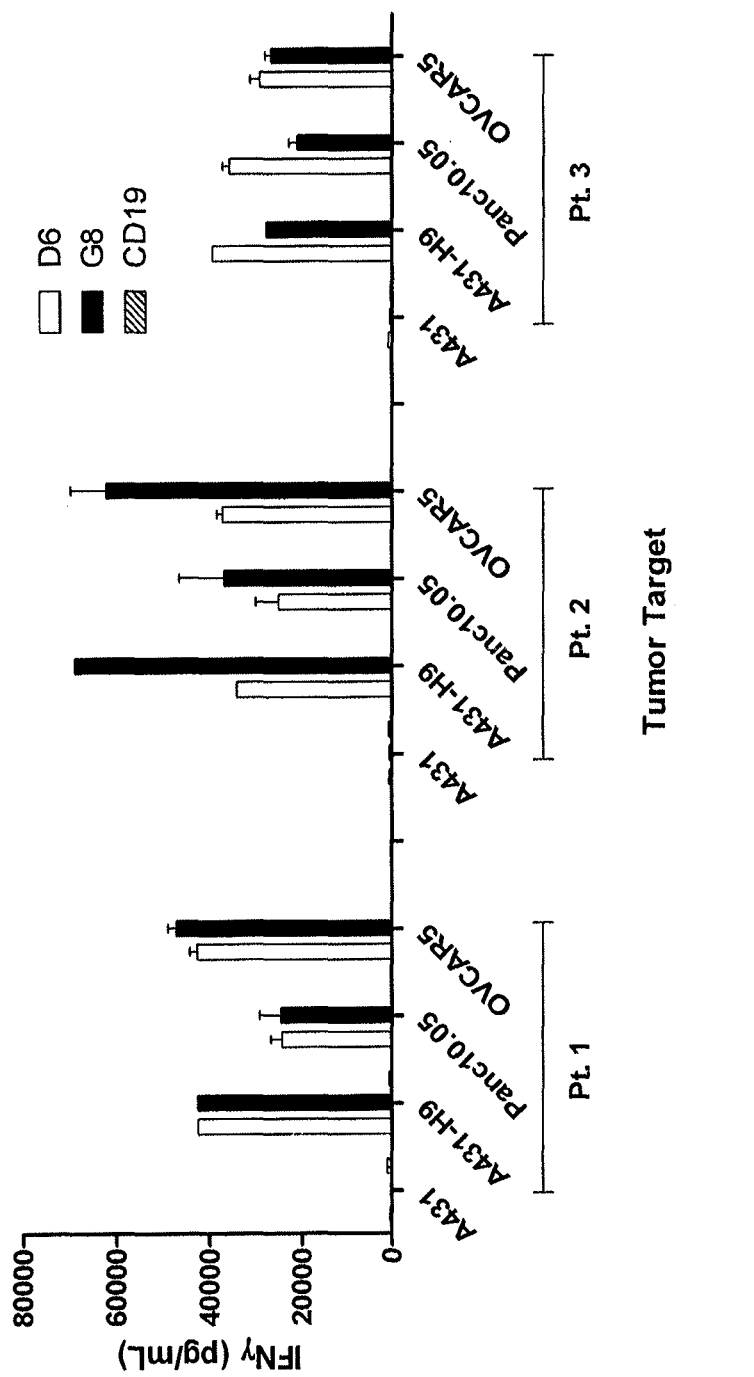

FIG. 2 is a graph showing interferon (IFN)-γ secretion (pg/ml) by peripheral blood lymphocytes (PBL) from each of three human donors (Pt.1, Pt. 2, and Pt. 3) transduced with codon-optimized SS1scFv-CD28Z CAR (SEQ ID NO: 29) (D6) (unshaded bars), codon-optimized SSscFv-CD28Z (SEQ ID NO: 27) (G8) (black bars), or anti-CD19 CAR (hatched bars) upon co-culture with target tumor cell lines A431, A431-H9, Panc10.05, or OVCAR5. FIG. 2 shows the function of CAR-transduced PBL following two stimulations with OKT3 (initial stimulation for transduction and a second stimulation during expansion of the numbers of cells).

DETAILED DESCRIPTION OF THE INVENTION

An embodiment of the invention provides chimeric antigen receptors (CARs) comprising (a) an antigen binding domain of HN1 or SS, a transmembrane domain, and an intracellular T cell signaling domain, or (b) an antigen binding domain of SS1, a transmembrane domain, an intracellular T cell signaling domain, and a granulocyte-macrophage colony-stimulating factor (GM-CSF) receptor 2 leader.

A chimeric antigen receptor (CAR) is an artificially constructed hybrid protein or polypeptide containing the antigen binding domain of an antibody (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response" as used herein means that the CAR can specifically bind to and immunologically recognize an antigen, such that binding of the CAR to the antigen elicits an immune response.

The CARs of the invention have antigen specificity for mesothelin. Mesothelin is expressed by normal, non-tumor, or non-cancerous mesothelial cells lining the pleura, peritoneum, and pericardium and is over-expressed by tumor or cancer cells from a variety of different cancers such as, e.g., ovarian cancer, pancreatic cancer, lung cancer (e.g., lung adenocarcinoma), esophageal cancer, gastric cancer, synovial sarcoma, and mesothelioma. The expression of mesothelin by normal, non-tumor, or non-cancerous cells is not as robust as the expression by tumor or cancer cells. In this regard, the tumor or cancer cells can over-express mesothelin or express mesothelin at a significantly higher level, as compared to the expression of mesothelin by normal, non-tumor, or non-cancerous cells.

Without being bound to a particular theory or mechanism, it is believed that by eliciting an antigen-specific response against mesothelin, the inventive CARs provide for one or more of the following: targeting and destroying mesothelin-expressing cancer cells, reducing or eliminating cancer cells, facilitating infiltration of immune cells to tumor site(s), and enhancing/extending anti-cancer responses.

The invention provides a CAR comprising an antigen binding domain of the antibody SS, SS1, or HN1. SS and SS1 are mouse antibodies that specifically recognize and bind to human mesothelin. HN1 is a human antibody that specifically recognizes and binds to human mesothelin. Exemplary suitable SS, SS1, and HN1 antibodies and portions thereof, including amino acid sequences thereof, are disclosed in U.S. Pat. Nos. 7,081,518; 7,709,252; 6,809,184, and WO 2010/111282, each of which is hereby incorporated by reference in its entirety. In this regard, a preferred embodiment of the invention provides CARs comprising an antigen-binding domain comprising, consisting of, or consisting essentially of, a single chain variable fragment (scFv) of SS, SS1, or HN1.

The scFv of SS, SS1, and HN1 comprises a light chain variable region and a heavy chain variable region. The light chain variable region may comprise, consist of, or consist essentially of any of SEQ ID NO: 1 (SS), SEQ ID NO: 2 (SS1), and SEQ ID NO: 3 (HN1). The heavy chain variable region may comprise, consist, or consist essentially of any of SEQ ID NO: 4 (SS), SEQ ID NO: 5 (SS1), and SEQ ID NO: 6 (HN1). Accordingly, in an embodiment of the invention, the antigen binding domain comprises an SS scFv comprising, consisting, or consisting essentially of SEQ ID NOs: 1 and 4, an SS1 scFv comprising, consisting, or consisting essentially of SEQ ID NOs: 2 and 5, or an HN1 scFv comprising, consisting, or consisting essentially of SEQ ID NOs: 3 and 6.

In an embodiment, the antigen binding domain comprises a linker. The linker connects the heavy chain variable region and the light chain variable region of the antigen binding domain. Any linker suitable for linking the heavy chain variable region and the light chain variable region may be used in the antigen binding domains of the invention. In an embodiment, the linker comprises, consists of, or consists essentially of SEQ ID NO: 7 or 8. Preferably, the antigen binding domain comprises a scFv comprising a heavy chain variable region, a light chain variable region, and a linker. In this regard, the antigen binding domain comprises, consists, or consists essentially of SEQ ID NO: 10 (SS), SEQ ID NO: 11 (SS1), or SEQ ID NO: 12 (HN1).

In an embodiment, the antigen binding domain comprises a leader sequence. The leader sequence may be positioned at the amino terminus of the light chain variable region. The leader sequence may comprise any suitable leader sequence. In an embodiment, the leader sequence is a human granulocyte-macrophage colony-stimulating factor (GM-CSF) receptor sequence. In this regard, the antigen binding domain comprises a leader sequence comprising, consisting of, or consisting essentially of SEQ ID NO: 9.

In an embodiment of the invention, the CAR comprises a transmembrane domain. In an embodiment of the invention, the transmembrane domain comprises i) CD8 and/or ii) CD28. In a preferred embodiment, the CD8 and CD28 are human. The CD8 or CD28 may comprise less than the whole CD8 or CD28, respectively. In this regard, the CAR comprises a CD8 transmembrane domain comprising, consisting of, or consisting essentially of SEQ ID NO: 13 and/or a CD28 transmembrane domain comprising, consisting of, or consisting essentially of SEQ ID NO: 14.

In an embodiment of the invention, the CAR comprises an intracellular T cell signaling domain comprising i) CD28, ii) CD137, and/or iii) CD3 zeta (ζ). In a preferred embodiment, the CD28, CD137, and CD3 zeta are human. CD28 is a T cell marker important in T cell co-stimulation. CD137, also known as 4-1BB, transmits a potent costimulatory signal to T cells, promoting differentiation and enhancing long-term survival of T lymphocytes. CD3 associates with TCRs to produce a signal and contains immunoreceptor tyrosine-based activation motifs (ITAMs). The CD28, CD137, or CD3 zeta may comprise less than the whole CD28, CD137, or CD3 zeta, respectively. In this regard, the intracellular T cell signaling domain comprises a CD28 amino acid sequence comprising, consisting of, or consisting essentially of, SEQ ID NO: 15, a CD137 amino acid sequence comprising, consisting of, or consisting essentially of, SEQ ID NO: 16 and/or a CD3 zeta amino acid sequence comprising, consisting of, or consisting essentially of, SEQ ID NO: 17.

In an embodiment of the invention, the CAR comprises a transmembrane domain comprising CD28 and an intracellular T cell signaling domain comprising CD28 and CD3 zeta. In this regard, the CAR may comprise each of SEQ ID NOs: 14, 15, and 17.

In an embodiment of the invention, the CAR comprises a transmembrane domain comprising CD8 and an intracellular T cell signaling domain comprising CD28, CD137, and CD3 zeta. In this regard, the CAR may comprise each of SEQ ID NOs: 13, 15, 16, and 17.

Additional embodiments of the invention provide CARs comprising, consisting of, or consisting essentially of any of, the amino acid sequences set forth in Table 1.

TABLE 1

| SEQ ID NO: | Antigen Binding Domain | Further Components |
|---|---|---|
| SEQ ID NO: 18 (SSscFv-CD28Z CAR) | SS | CD28 transmembrane domain CD28 and CD3ζ intracellular T cell signaling domains |
| SEQ ID NO: 19 (SSscFv-CD28BBZ CAR) | SS | CD8 transmembrane domain CD28, CD137, and CD3ζ intracellular T cell signaling domains |
| SEQ ID NO: 20 (SS1scFv-28Z CAR) | SS1 | CD28 transmembrane domain CD28 and CD3ζ intracellular T cell signaling domains |
| SEQ ID NO: 21 (SS1scFv-28BBZ CAR) | SS1 | CD8 transmembrane domain CD28, CD137, and CD3ζ intracellular T cell signaling domains |
| SEQ ID NO: 22 (HN1scFv-28Z CAR) | HN1 | CD28 transmembrane domain CD28 and CD3ζ intracellular T cell signaling domains |
| SEQ ID NO: 23 (HN1scFv-28BBZ CAR) | HN1 | CD8 transmembrane domain CD28, CD137, and CD3ζ intracellular T cell signaling domains |

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs of embodiments of the invention (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive CARs can be synthetic, recombinant, isolated, and/or purified.

An embodiment of the invention further provides an antibody, or antigen binding portion thereof, which specifically binds to an epitope of the CARs of the invention. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive CAR.

Methods of testing antibodies for the ability to bind to any functional portion of the inventive CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338,929).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, $5^{th}$ Ed., Garland Publishing, New York, N.Y. (2001)). Alternatively, other methods, such as EBV-hybridoma methods (Haskard and Archer, *J. Immunol. Methods,* 74(2), 361-67 (1984), and Roder et al., *Methods Enzymol.,* 121, 140-67 (1986)), and bacteriophage vector expression systems (see, e.g., Huse et al., *Science,* 246, 1275-81 (1989)) are known in the art. Further, methods of producing antibodies in non-human animals are described in, e.g., U.S. Pat. Nos. 5,545,806, 5,569,825, and 5,714,352, U.S. Patent Application Publication No. 2002/0197266 A1, and U.S. Pat. No. 7,338,929).

Phage display furthermore can be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.,* 235, 959-973 (1994).

An embodiment of the invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering,* 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Further provided by an embodiment of the invention is a nucleic acid comprising a nucleotide sequence encoding any of the CARs described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-optimized. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-optimized nucleotide sequence that encodes the antigen binding domain of the inventive CAR. In this regard, the nucleic acid may comprise, consist of, or consist essentially of SEQ ID NO: 24 (SS scFv), SEQ ID NO: 25 (SS1 scFv), or SEQ ID NO: 26 (HN1 scFv).

In another embodiment of the invention, the nucleic acid may comprise a codon-optimized nucleotide sequence that encodes any of the CARs described herein (including functional portions and functional variants thereof). In this regard, an embodiment of the invention provides nucleic acids comprising, consisting of, or consisting essentially of the nucleotide sequences of Table 2:

TABLE 2

| SEQ ID NO: | Antigen Binding Domain | Further Components |
|---|---|---|
| SEQ ID NO: 27 (SSscFv-CD28Z CAR) | SS | CD28 transmembrane domain CD28 and CD3ζ intracellular T cell signaling domains |
| SEQ ID NO: 28 (SSscFv-CD28BBZ CAR) | SS | CD8 transmembrane domain CD28, CD137, and CD3ζ intracellular T cell signaling domains |
| SEQ ID NO: 29 (SS1scFv-28Z CAR) | SS1 | CD28 transmembrane domain CD28 and CD3ζ intracellular T cell signaling domains |
| SEQ ID NO: 30 (SS1scFv-28BBZ CAR) | SS1 | CD8 transmembrane domain CD28, CD137, and CD3ζ intracellular T cell signaling domains |
| SEQ ID NO: 31 (HN1scFv-28Z CAR) | HN1 | CD28 transmembrane domain CD28 and CD3ζ intracellular T cell signaling domains |
| SEQ ID NO: 32 (HN1scFv-28BBZ CAR) | HN1 | CD8 transmembrane domain CD28, CD137, and CD3ζ intracellular T cell signaling domains |

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature, conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. In a preferred embodiment, the recombinant expression vector is a gammaretroviral vector. Without being bound to a particular theory, it is believed that gammaretroviral vectors advantageously facilitate the generation of a stable packaging cell line which can be used to generate a master cell bank and vector supernatant more efficiently as compared to lentiviral vectors.

A number of transfection techniques are generally known in the art (see, e.g., Graham et al., *Virology*, 52: 456-467 (1973); Sambrook et al., supra; Davis et al., *Basic Methods in Molecular Biology*, Elsevier (1986); and Chu et al., *Gene*, 13: 97 (1981). Transfection methods include calcium phosphate co-precipitation (see, e.g., Graham et al., supra), direct micro injection into cultured cells (see, e.g., Capecchi, *Cell*, 22: 479-488 (1980)), electroporation (see, e.g., Shigekawa et al., *BioTechniques*, 6: 742-751 (1988)), liposome mediated gene transfer (see, e.g., Mannino et al., *BioTechniques*, 6: 682-690 (1988)), lipid mediated transduction (see, e.g., Feigner et al., *Proc. Natl. Acad. Sci. USA*, 84: 7413-7417 (1987)), and nucleic acid delivery using high velocity microprojectiles (see, e.g., Klein et al., *Nature*, 327: 70-73 (1987)).

In an embodiment, the recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Included in the scope of the invention are conjugates, e.g., bioconjugates, comprising any of the inventive CARs (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naïve T cells, and the like. The T cell may be a $CD8^+$ T cell or a $CD4^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the CARs, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive CAR materials can comprise more than one inventive CAR material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

The inventive CAR materials can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive CAR material in the pharmaceutical formulations can vary, e.g., from less than about 1%, usually at or at least about 10%, to as much as about 20% to about 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, Remington: The Science and Practice of Pharmacy, Lippincott Williams & Wilkins; 21st ed. (May 1, 2005).

The following formulations for oral, aerosol, parenteral (e.g., subcutaneous, intravenous, intraarterial, intramuscular, intradermal, interperitoneal, and intrathecal), and topical administration are merely exemplary and are in no way limiting. More than one route can be used to administer the inventive CAR materials, and in certain instances, a particular route can provide a more immediate and more effective response than another route.

Formulations suitable for oral administration can comprise or consist of (a) liquid solutions, such as an effective amount of the inventive CAR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive CAR material in a flavor, usually sucrose and acacia or tragacanth, as well as pastilles comprising the inventive CAR material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The inventive CAR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive CAR material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations, including those that are useful for transdermal drug release, are well known to those of skill in the art and are suitable in the context of embodiments of the invention for application to skin. The inventive CAR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR materials in each or various rounds of administration. By way of example and not intending to limit the invention, the dose of the inventive CAR material can be about 0.001 to about 1000 mg/kg body weight of the subject being treated/day, from about 0.01 to about 10 mg/kg body weight/day, about 0.01 mg to about 1 mg/kg body weight/day. In an embodiment of the invention, the dose may be from about $1 \times 10^4$ to about $1 \times 10^8$ cells expressing the inventive CAR material per kg body weight. When the inventive CAR material is a host cell, an exemplary dose of host cells may be a minimum of one million cells (1 mg cells/dose). When the inventive CAR material is a nucleic acid packaged in a virus, an exemplary dose of virus may be 1 ng/dose.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

In addition to the aforedescribed pharmaceutical compositions, the inventive CAR materials can be formulated as inclusion complexes, such as cyclodextrin inclusion complexes, or liposomes. Liposomes can serve to target the inventive CAR materials to a particular tissue. Liposomes also can be used to increase the half-life of the inventive CAR materials. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

One of ordinary skill in the art will readily appreciate that the inventive CAR materials of the invention can be modified in any number of ways, such that the therapeutic or prophylactic efficacy of the inventive CAR materials is increased through the modification. For instance, the inventive CAR materials can be conjugated either directly or indirectly through a linking moiety to a targeting moiety. The practice of conjugating compounds, e.g., inventive CAR materials, to targeting moieties is known in the art. See, for instance, Wadwa et al., *J. Drug Targeting* 3: 111 (1995) and U.S. Pat. No. 5,087,616.

Alternatively, the inventive CAR materials can be modified into a depot form, such that the manner in which the inventive CAR materials is released into the body to which it is administered is controlled with respect to time and location within the body (see, for example, U.S. Pat. No. 4,450,150). Depot forms of inventive CAR materials can be, for example, an implantable composition comprising the inventive CAR materials and a porous or non-porous material, such as a polymer, wherein the inventive CAR materials are encapsulated by or diffused throughout the material and/or degradation of the non-porous material. The depot is then implanted into the desired location within the body and the inventive CAR materials are released from the implant at a predetermined rate.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously. An exemplary therapeutic agent that can be co-administered with the CAR materials is IL-2. It is believed that IL-2 enhances the therapeutic effect of the inventive CAR materials. Without being bound by a particular theory or mechanism, it is believed that IL-2 enhances therapy by enhancing the in vivo expansion of the numbers of cells expressing the inventive CARs. For purposes of the inventive methods, wherein host cells or populations of cells are administered to the mammal, the cells can be cells that are allogeneic or autologous to the mammal.

It is contemplated that the inventive CARs materials can be used in methods of treating or preventing a disease in a mammal. Without being bound to a particular theory or mechanism, the inventive CARs have biological activity, e.g., ability to recognize antigen, e.g., mesothelin, such that the CAR when expressed by a cell is able to mediate an immune response against the cell expressing the antigen, e.g., mesothelin, for which the CAR is specific. In this regard, an embodiment of the invention provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions of the invention in an amount effective to treat or prevent cancer in the mammal.

An embodiment of the invention further comprises lymphodepleting the mammal prior to administering the inventive CAR materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer. Preferably, the cancer is ovarian cancer, pancreatic cancer, lung cancer (e.g., lung adenocarcinoma), esophageal cancer, gastric cancer, synovial sarcoma, or mesothelioma. Preferably, the cancer is characterized by the expression of mesothelin.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions of the invention, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive CARs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing a CAR for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor α (TNF-α) or interleukin 2 (IL-2)). In addition, CAR function can be evaluated by measurement of cellular cytoxicity, as described in Zhao et al., *J. Immunol.*, 174: 4415-4423 (2005).

Another embodiment of the invention provides the use of the CARs, nucleic acids, recombinant expression vectors, host cells, populations of cells, antibodies, or antigen binding portions thereof, and/or pharmaceutical compositions of the invention, for the treatment or prevention of cancer in a mammal. The cancer may be any of the cancers described herein. Preferably, the cancer is ovarian cancer, pancreatic cancer, lung cancer (e.g., lung adenocarcinoma), esophageal cancer, gastric cancer, synovial sarcoma, or mesothelioma.

The following examples further illustrate the invention but, of course, should not be construed as in any way limiting its scope.

Example 1

This example demonstrates the function of human peripheral blood lymphocytes (PBL) transduced with codon-optimized SS1scFv-CD28Z CAR, SS1scFv-CD28BBZ CAR, HN1scFv-28Z, or HN1scFv-28BBZ.

PBL from three human donors were untransduced or transduced with codon-optimized SS1scFv-CD28Z CAR (SEQ ID NO: 29), SS1scFv-CD28BBZ CAR (SEQ ID NO: 30), HN1scFv-28Z (SEQ ID NO: 31), or HN1scFv-28BBZ (SEQ ID NO: 32). The PBL were initially exposed to or stimulated by OKT3 (S1) in order to achieve efficient CAR transduction. The cells were then analyzed for CAR expression and function as measured by IFN-γ release on day 7 (d7) (S1d7). The percentage of cells expressing the CAR was measured by fluorescence-activated cell sorting (FACS) (Tables 3A-3C). Effector untransduced or transduced cells were co-cultured with target A431 cells (epidermoid carcinoma; mesothelin negative), Mel938 (melanoma; mesothelin negative), or mesothelin-expressing target tumor cell line A431-H9 (human mesothelin-transfected A431 cell line (epidermoid cancer)) or HAY (mesothelioma) at an effector:target ratio of 1:10. Upon co-culture, interferon (IFN)-γ secretion was measured (Tables 3A-3C). In Tables 3A-3C, "transient" refers to vector supernatant generated by transient transfection of 293GP cells. "Clinical" refers to clinical supernatant, which was generated from the PG13 packaging cell line. The data presented in Tables 3A-C are pre-clinical data evaluating the different constructs.

TABLE 3A

| | Patient 1 | | | | |
|---|---|---|---|---|---|
| | | IFN-γ (pg/ml) | | | |
| | S1d7FACS % CAR+ | A431-H9 | A431 | HAY | Mel938 |
| Untransduced (UT) | 1.1 | <33 | <33 | <33 | <33 |
| Clinical coSS1scFv-CD28Z supernatant | 42.7 | 5628 | 83 | 6703 | 85 |
| Transient coSS1scFv-CD28Z | 78.2 | 15265 | 258 | 15376 | 244 |
| Transient coSS1scFv-CD28BBZ | 12.7 | 1028 | 31 | 2258 | 32 |

TABLE 3A-continued

Patient 1

|  | S1d7FACS % CAR+ | A431-H9 | A431 | HAY | Mel938 |
|---|---|---|---|---|---|
| Transient coHN1scFv-CD28Z | 88 | 7597 | 868 | 8845 | 800 |
| Transient coHN1scFv-CD28BBZ | 27.7 | 9176 | 49 | 5144 | 42 |

TABLE 3B

Patient 2

|  | S1d7FACS % CAR+ | A431-H9 | A431 | HAY | Mel938 |
|---|---|---|---|---|---|
| UT | 2.2 | <33 | <33 | <33 | <33 |
| Clinical coSS1scFv-28Z supernatant | 53.5 | 2635 | 165 | 5270 | 165 |
| Transient coSS1scFv-CD28Z | 79.7 | 22639 | 236 | 21850 | 228 |
| Transient coSS1scFv-CD28BBZ | 44 | 349 | 113 | 1103 | 110 |
| Transient coHN1scFv-28Z | 79.1 | 20817 | 762 | 20651 | 710 |
| Transient coHN1scFv-28BBZ | 17.9 | 9480 | 143 | 6365 | 146 |

TABLE 3C

Patient 3

|  | S1d7FACS % CAR+ | A431-H9 | A431 | HAY | Mel938 |
|---|---|---|---|---|---|
| UT | 1.4 | 46 | <33 | <33 | <33 |
| Clinical coSS1scFv-28Z supernatant | 44.5 | 6343 | 56 | 5356 | 244 |
| Transient coSS1scFv-CD28Z | 23.6 | 1927 | 93 | 1338 | 315 |
| Transient coSS1scFv-CD28BBZ | 18.1 | 303 | 76 | 286 | 101 |
| Transient coHN1scFv-28Z | 95.1 | 8492 | 78 | 10210 | 101 |
| Transient coHN1scFv-28BBZ | 74.6 | 8729 | 51 | 2851 | 111 |

As shown in Tables 3A-3C, human PBL transduced with codon-optimized SS1scFv-CD28Z CAR, SS1scFv-CD28BBZ CAR, HN1scFv-28Z, or HN1scFv-28BBZ were reactive with one or more mesothelin-expressing tumor cell lines (A431-H9 or HAY cells) as measured by IFN-γ secretion.

Example 2

This example demonstrates the mesothelin-specific degranulation of cells transduced with codon-optimized SS1scFv-CD28Z CAR.

Lysosomal-associated membrane protein-1 (LAMP-1 or CD107a) has been described as a marker of antigen-specific T-cell degranulation or lysis. Alter et al., *J. Immunol. Methods*, 294: 15-22 (2004). The expression of CD107a by PBL that were untransduced or transduced with codon-optimized SS1scFv-CD28Z CAR (SEQ ID NO: 29) was measured by FACS after co-culture with A431 cells, A431-H9 cells, or PMA/ionomycin.

The data showed that CAR-transduced PBL upregulated CD107a, a marker of degranulation, only when they encountered specific antigen, which is expressed by the A431-H9 cells. CAR-transduced PBL did not upregulate CD107a in response to co-culture with A431 (antigen negative) cells. PMA/ionomycin was used as a positive control. Co-culture with PMA/ionomycin showed that all CAR-transduced cells were able to up-regulate CD107a when stimulated non-specifically. Taken together, these data showed that the SS1scFv-CD28Z CAR-transduced PBL specifically recognize mesothelin on the surface of A431-H9 cells.

Example 3

This example demonstrates the function of cells transduced with a gammaretroviral vector encoding codon-optimized SS1scFv-CD28Z CAR.

Phoenix-ECO vector packaging cell lines were used to make a working cell bank. These cells were transiently transfected with gammaretroviral transfer vectors including SS1scFv-CD28Z CAR (SEQ ID NO: 29). The vector supernatant was used to transduce PG13 packaging cells for the generation of a stable gammaretroviral packaging clones. The selected cell PG13 clone was used to generate a master cell bank that constitutively produced retroviral vector particles. The master cell bank was then fully characterized and tested for biosafety before being used to generate a clinical-grade retroviral vector supernatant. The titer from six vector harvests was measured and is shown in Table 4A. All six harvests were from the D6 packaging clone encoding the coSS1scFv-CD28Z CAR.

PBL from three patients (K, L, and M) were transduced with vector supernatant from each of the six harvests and subjected to an IFN-γ release assay. All harvests were tested for the ability to transduce the 3 patients' PBL. The results are shown in Table 4B.

TABLE 4A

| | Vector Harvest | | | | | |
|---|---|---|---|---|---|---|
| | 1 | 2 | 3 | 4 | 5 | 6 |
| Titer (Tu/mL, ×10$^6$) | 1.2 ± 0.2 | 1.8 ± 0.1 | 1.2 ± 0.2 | 2.2 ± 0.2 | 1.8 ± 0.2 | 1.8 ± 0.1 |

TABLE 4B

| Patient | Cell Line | Mesothelin Expression | IFN-γ (pg/ml) | | | | | |
|---|---|---|---|---|---|---|---|---|
| | | | 1 | 2 | 3 | 4 | 5 | 6 |
| Pt. K | None | − | 634 | 583 | 705 | 642 | 657 | 451 |
| Pt. L | | | 112 | 113 | 98 | 101 | 87 | 102 |
| Pt. M | | | 102 | 94 | 91 | 86 | 116 | 108 |
| Pt. K | A431 | − | 174 | 162 | 194 | 188 | 193 | 132 |
| Pt. L | | | 118 | 108 | 104 | 100 | 135 | 128 |
| Pt. M | | | 87 | 94 | 80 | 84 | 75 | 84 |
| Pt. K | A431-H9 | + | 16269 | 30225 | 32773 | 32580 | 23620 | 20308 |
| Pt. L | | | 32775 | 28481 | 36661 | 36893 | 36635 | 29288 |
| Pt. M | | | 5686 | 10049 | 15035 | 14103 | 9357 | 9831 |
| Pt. K | HAY | + | 13476 | 26808 | 30111 | 25345 | 19965 | 16231 |
| Pt. L | | | 3958 | 8256 | 9200 | 9903 | 5100 | 4314 |
| Pt. M | | | 20680 | 23260 | 26672 | 24536 | 25168 | 18134 |
| Pt. K | OVCAR3 | + | 21020 | 37398 | 40249 | 32130 | 27088 | 21800 |
| Pt. L | | | 2721 | 4486 | 4656 | 4700 | 2718 | 2597 |
| Pt. M | | | 26210 | 16337 | 20740 | 22784 | 21669 | 16410 |

As shown in Table 4B, human PBL transduced with a gammaretroviral vector including codon-optimized SS1scFv-CD28Z CAR were reactive with one or more mesothelin-expressing tumor cell lines as measured by IFN-γ secretion.

Example 4

This example demonstrates the function of human PBL transduced with codon-optimized SS1scFv-CD28Z CAR or SSscFv-CD28Z CAR.

PBL from three human donors were untransduced (UT) or transduced with codon-optimized SS1scFv-CD28Z CAR (SEQ ID NO: 29) (from PG13 packaging clone D6 or D8) or SSscFv-CD28Z CAR (SEQ ID NO: 27) (from PG13 packaging clone C2 or G8). Untransduced or transduced cells were co-cultured with A431, A431-H9, OVACAR3, or Panc10.05 cells. IFN-γ secretion was measured (FIG. 1). FIG. 1 shows the function of CAR-transduced PBL following initial stimulation with OKT3 during transduction (S1d7). As shown in FIG. 1, human PBL transduced with codon-optimized SS1scFv-CD28Z CAR or SSscFv-CD28Z CAR were reactive with one or more mesothelin-expressing tumor cell lines (A431-H9, OVACAR3, or Panc10.05 cells) as measured by IFN-γ secretion.

Example 5

This example demonstrates the function of expanded numbers of human PBL transduced with codon-optimized SS1scFv-CD28Z CAR or codon-optimized SSscFv-CD28Z CAR.

The numbers of human PBL from three donors that were transduced with an anti-CD19 CAR (control), codon-optimized SSscFv-CD28Z CAR, or codon-optimized SS1scFv-CD28Z CAR, as described in Example 4, were subjected to a secondary OKT3 stimulation and expansion. The numbers of PBL were expanded as described in Riddell et al., Science, 257:238-241 (1992) and Dudley et al., Cancer J. Sci. Am., 6:69-77 (2000). Generally, the numbers of PBL are expanded up to 3 logs using soluble OKT3, irradiated feeder cells, and high-dose IL-2. Up to about $1 \times 10^{10}$ to about $1 \times 10^{11}$ or more cells may be generated for patient treatment.

Expression of anti-CD19 CAR, SSscFv-CD28Z CAR, or SS1scFv-CD28Z CAR was confirmed by FACS. Fold expansion of the numbers of cells was measured. As shown in Table 5, the numbers of PBL transduced with codon-optimized SS1scFv-CD28Z CAR increased about 100-fold.

TABLE 5

| | | Fold Expansion |
|---|---|---|
| Patient 1 | SS1scFv-CD28Z CAR | 98 |
| | SSscFv-CD28Z CAR | 93 |
| | anti-CD19 CAR | 98 |
| Patient 2 | SS1scFv-CD28Z CAR | 95 |
| | SSscFv-CD28Z CAR | 94 |
| | anti-CD19 CAR | 96 |
| Patient 3 | SS1scFv-CD28Z CAR | 98 |
| | SSscFv-CD28Z CAR | 87 |
| | anti-CD19 CAR | 94 |

Expanded numbers of cells were co-cultured with mesothelin-expressing target tumor cell lines A431-H9, A431, Panc10.05 (pancreatic), or OVCAR5 (ovarian). Interferon (IFN)-γ secretion was measured. As shown in FIG. 2, expanded numbers of PBL transduced with SS1scFv-CD28Z CAR (from PG13 packaging clone D6) or SSscFv-CD28Z CAR (from PG13 packaging clone G8) were reactive with one or more mesothelin-expressing tumor cell lines as measured by IFN-γ secretion. These data show that after expansion of the numbers of CAR-transduced PBL, both CAR surface expression and function are maintained.

Example 6

This example demonstrates the treatment of cancer patients by administering PBL transduced with SS1 scFv-CD28Z CAR.

Eligibility:

Eligible patients have metastatic or unresectable cancer that expresses mesothelin and either did not respond to standard care or their cancer recurred after standard care.

Design:

Patients with mesothelioma tumors, pancreatic tumors, or mesothelin-positive tumors as determined by immunohistochemistry (IHC) or reverse transcriptase polymerase chain reaction (RT-PCR) are accrued into the Phase I portion of the study. Patients receive a nonmyeloablative lypmphodepleting regimen, anti-mesothelin CAR engineered PBL, and aldesleukin. The maximum tolerated dose (MTD) is determined in Phase I and applied to the Phase II study.

In Phase II, patients are entered into two cohorts based on histology: cohort 1 includes patients with mesothelioma, and cohort 2 includes patients with all other cancer types that express mesothelin.

Phase I Dose Escalation:

The protocol enrolls 1 patient in each dose cohort. If there is a Dose Limiting Toxicity (DLT), the cohort expands to 6 patients. The total number of anti-mesothelin CAR engineered cells transferred for each cohort is set forth in Table 6:

TABLE 6

| Cohort 1 | $10^6$ cells |
|---|---|
| Cohort 2 | $3 \times 10^6$ cells |
| Cohort 3 | $10^7$ cells |
| Cohort 4 | $3 \times 10^7$ cells |
| Cohort 5 | $10^8$ cells |
| Cohort 6 | $3 \times 10^8$ cells |
| Cohort 7 | $10^9$ cells |
| Cohort 8 | $3 \times 10^9$ cells |
| Cohort 9 | $10^{10}$ cells |

Clinical tumor regression is evaluated in the treated patients. The safety of administering anti-mesothelin CAR engineered PBL to patients receiving a nonmyeloablative conditioning regimen and aldesleukin is also determined. The in vivo survival of CAR gene-engineered cells is also evaluated.

Example 7

This example demonstrates the function of PBL transduced with codon-optimized SSscFv-CD28Z CAR or SSscFv-CD28BBZ CAR.

PBL from three human donors (Patients (Pt.) I, M, and T) were untransduced (UT) or transduced with codon-optimized SSscFv-CD28Z CAR (SEQ ID NO: 27) or SSscFv-CD28BBZ CAR (SEQ ID NO: 28). The PBL were initially exposed to or stimulated by OKT3 (S1) in order to achieve efficient CAR transduction. The cells were then analyzed for CAR expression and function as measured by IFN-γ release on day 7 (d7) (S1d7). The percentage of cells expressing the CAR was measured by fluorescence-activated cell sorting (FACS) (Tables 7A-7C). Effector untransduced or transduced cells were cultured in media or co-cultured with target A431 cells (epidermoid carcinoma; mesothelin negative), Mel624 (melanoma; meosthelin negative), or mesothelin-expressing target tumor cell line A431-H9 (human mesothelin-transfected A431 cell line (epidermoid cancer)) or You (mesothelioma) at an effector:target ratio of 1:10. Upon co-culture, interferon (IFN)-γ secretion was measured (Tables 7A-7C).

TABLE 7A

Patient I

| | S1d7FACS % CAR+ | IFN-γ (pg/ml) | | | | |
|---|---|---|---|---|---|---|
| | | A431 | A431-H9 | You | Mel624 | Media |
| UT | 0 | 12 | 0 | 0 | 35 | 29 |
| coSSscFv-28BBZ | 60 | 52 | 1460 | 8890 | 62 | 55 |
| coSSscFv-28Z | 74 | 656 | 13136 | 24684 | 664 | 689 |

TABLE 7B

Patient M

| | S1d7FACS % CAR+ | IFN-γ (pg/ml) | | | | |
|---|---|---|---|---|---|---|
| | | A431 | A431-H9 | You | Mel624 | Media |
| UT | 0 | 36 | 16 | 23 | 40 | 65 |
| coSSscFv-28BBZ | 62 | 55 | 6010 | 6800 | 61 | 77 |
| coSSscFv-28Z | 77 | 385 | 19117 | 27713 | 383 | 465 |

TABLE 7C

Patient T

| | S1d7FACS % CAR+ | IFN-γ (pg/ml) | | | | |
|---|---|---|---|---|---|---|
| | | A431 | A431-H9 | You | Mel624 | Media |
| UT | 0 | 21 | 0 | 0 | 0 | 56 |
| coSSscFv-28BBZ | 62 | 81 | 2309 | 11990 | 97 | 114 |
| coSSscFv-28Z | 77 | 259 | 10741 | 19197 | 247 | 293 |

As shown in Tables 7A-7C, human PBL transduced with codon-optimized SSscFv-CD28Z CAR or SSscFv-CD28BBZ CAR were reactive with one or more mesothelin-expressing tumor cell lines (A431-H9 or You cells) as measured by IFN-γ secretion.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A chimeric antigen receptor (CAR) comprising:
    (a) an antigen binding domain of HN1 or SS, a transmembrane domain, and an intracellular T cell signaling domain, or
    (b) an antigen binding domain of SS1, a transmembrane domain, an intracellular T cell signaling domain, and a granulocyte-macrophage colony-stimulating factor (GM-CSF) receptor 2 leader.

2. The CAR according to claim 1, wherein the antigen binding domain comprises a light chain variable region comprising any one of SEQ ID NOs: 1-3.

3. The CAR according to claim 1, wherein the antigen binding domain comprises a heavy chain variable region comprising any one of SEQ ID NOs: 4-6.

4. The CAR according to claim 1, wherein the antigen binding domain comprises a linker comprising SEQ ID NO: 7 or 8.

5. The CAR according to claim 1, wherein the antigen binding domain comprises a leader sequence comprising SEQ ID NO: 9.

6. The CAR according to claim 1, wherein the antigen binding domain comprises any one of SEQ ID NOs: 10-12.

7. The CAR according to claim 1, wherein the transmembrane domain comprises i) CD8 and/or ii) CD28.

8. The CAR according to claim 1, wherein the transmembrane domain comprises a CD8 amino acid sequence comprising SEQ ID NO: 13 and/or a CD28 amino acid sequence comprising SEQ ID NO: 14.

9. The CAR according to claim 1, wherein the intracellular T cell signaling domain comprises i) CD28, ii) CD137, and/or iii) CD3 zeta.

10. The CAR according to claim 1, wherein the intracellular T cell signaling domain comprises a CD28 amino acid sequence comprising SEQ ID NO: 15.

11. The CAR according to claim 1, wherein the intracellular T cell signaling domain comprises a CD137 amino acid sequence comprising SEQ ID NO: 16.

12. The CAR according to claim 1, wherein the intracellular T cell signaling domain comprises a CD3 zeta amino acid sequence comprising SEQ ID NO: 17.

13. The CAR according to claim 1, comprising any one of SEQ ID NOs: 18-23.

14. A nucleic acid comprising a nucleotide sequence encoding the CAR according to claim 1.

15. The nucleic acid according to claim 14, wherein the nucleotide sequence is codon-optimized.

16. The nucleic acid according to claim 14, comprising a nucleotide sequence selected from the group consisting of SEQ ID NOs: 24-26.

17. The nucleic acid according to claim 14, comprising a nucleotide sequence selected from the group consisting of SEQ ID NOs: 27-32.

18. A recombinant expression vector comprising the nucleic acid according to claim 14.

19. The recombinant expression vector according to claim 18, wherein the recombinant expression vector is a gammaretroviral vector.

20. An isolated host cell comprising the recombinant expression vector of claim 18.

21. A population of cells comprising at least one host cell of claim 20.

22. An antibody, or antigen binding portion thereof, which specifically binds to a CAR according to claim 1.

23. A pharmaceutical composition comprising the CAR of claim 1 and a pharmaceutically acceptable carrier.

24. A method of detecting the presence of cancer, comprising:
   (a) contacting a sample comprising one or more cells with the CAR of claim 1, thereby forming a complex, and
   (b) detecting the complex, wherein detection of the complex is indicative of the presence of cancer.

25. The method of claim 24, wherein the cancer is ovarian cancer, pancreatic cancer, lung cancer, esophageal cancer, gastric cancer, synovial sarcoma, or mesothelioma.

26. A method of treating or preventing cancer in a mammal, the method comprising administering the CAR of claim 1 to the mammal in an amount effective to treat or prevent cancer in the mammal.

27. The method of claim 26, wherein the cancer is ovarian cancer, pancreatic cancer, lung cancer, esophageal cancer, gastric cancer, synovial sarcoma, or mesothelioma.

\* \* \* \* \*